US008361000B2

(12) United States Patent
Gaspard

(10) Patent No.: US 8,361,000 B2
(45) Date of Patent: *Jan. 29, 2013

(54) AUTOMATED INFANT MASSAGER

(76) Inventor: Sanna Gaspard, Pittsburgh, PA (US)

( * ) Notice: Subject to any disclaimer, the term of this patent is extended or adjusted under 35 U.S.C. 154(b) by 865 days.

This patent is subject to a terminal disclaimer.

(21) Appl. No.: 12/504,809

(22) Filed: Jul. 17, 2009

(65) Prior Publication Data

US 2010/0030122 A1 Feb. 4, 2010

Related U.S. Application Data

(63) Continuation-in-part of application No. 12/051,906, filed on Mar. 20, 2008, now Pat. No. 8,142,375.

(60) Provisional application No. 60/908,749, filed on Mar. 29, 2007.

(51) Int. Cl.
*A61B 5/00* (2006.01)
(52) U.S. Cl. ............... 601/84; 600/300; 600/22; 606/1
(58) Field of Classification Search ............... None
See application file for complete search history.

(56) References Cited

U.S. PATENT DOCUMENTS

| | | | |
|---|---|---|---|
| 3,290,985 A | 12/1966 | Bains et al. |
| 3,802,420 A | 4/1974 | Moffat et al. |
| 3,994,290 A | 11/1976 | Springer et al. |
| 4,088,124 A | 5/1978 | Korner et al. |
| 4,191,177 A | 3/1980 | Abbott |
| 4,681,096 A | 7/1987 | Cuervo |
| 4,754,747 A | 7/1988 | Hasofer |
| 4,777,945 A | 10/1988 | Curtaz et al. |
| 4,834,075 A | 5/1989 | Guo et al. |
| 5,006,105 A | 4/1991 | Sherard |
| 5,052,377 A | 10/1991 | Frajdenrajch |
| 5,054,472 A | 10/1991 | Stefan |
| 5,063,912 A | 11/1991 | Hughes |
| 5,125,399 A | 6/1992 | Tarjoto |
| 5,446,934 A | 9/1995 | Frazier |
| 5,505,691 A | 4/1996 | Fenkell |
| 5,820,573 A | 10/1998 | Ramos |

(Continued)

FOREIGN PATENT DOCUMENTS

WO 2009049245 A1 4/2009

OTHER PUBLICATIONS

Tiffany Field et al., "Massage of Preterm Newborns to Improve Growth and Development", Pediatric Nursing, Nov./Dec. 1987, vol. 13/No. 6, Antony J. Jannetti, Inc. Publication, USA, pp. 385-387.

(Continued)

*Primary Examiner* — Aaron Roane
*Assistant Examiner* — Lynsey Crandall
(74) *Attorney, Agent, or Firm* — Eckert Seamans Cherin & Mellott, LLC; Arnold B. Silverman

(57) ABSTRACT

An automated infant massager system that monitors an infant's physical, physiological and behavioral response to the massage and can adjust the intensity of the massage and massager duration settings based on the responses of the infant and/or information from a user, preferably autonomously. A processor, which is operatively associated with the infant massager, coordinates overall operations and functions of the infant massager, as well as receiving information regarding the infant's physical, behavioral, and physiological responses to the massage. The user input through the remote receiver transmitter, and/or an associated bar code/radio-frequency identification (RFID) scanner, and/or direct communications with the processor may be employed. In a further embodiment of the present invention, a plurality of infant massaging units are controlled in network fashion by means of a processor and router, thereby permitting one or more infant massagers to be controlled by one or more users and allows one or more automated infant massagers to communicate and interface with electronic medical record (EMR) systems.

45 Claims, 20 Drawing Sheets

U.S. PATENT DOCUMENTS

| | | | |
|---|---|---|---|
| 5,853,005 | A | 12/1998 | Scanlon |
| 5,951,501 | A | 9/1999 | Griner |
| 6,052,852 | A | 4/2000 | Huang |
| 6,142,963 | A | 11/2000 | Black et al. |
| 6,175,981 | B1 | 1/2001 | Lizama et al. |
| 6,402,709 | B1 | 6/2002 | Wu |
| 6,409,654 | B1 | 6/2002 | McClain |
| 6,454,731 | B1 | 9/2002 | Marcantoni |
| 6,478,755 | B2 | 11/2002 | Young |
| 6,544,173 | B2 | 4/2003 | West et al. |
| 6,751,499 | B2 | 6/2004 | Lange et al. |
| 6,757,598 | B2 | 6/2004 | Okoshi |
| 6,814,709 | B2 | 11/2004 | Schwartz et al. |
| 7,004,916 | B2 | 2/2006 | Dehli |
| 7,175,592 | B2 | 2/2007 | Lee |
| 7,322,946 | B2 | 1/2008 | Lev et al. |
| 2002/0033628 | A1 | 3/2002 | Clough |
| 2002/0145512 | A1 | 10/2002 | Sleichter, III et al. |
| 2003/0212352 | A1 | 11/2003 | Kahn |
| 2005/0151401 | A1 | 7/2005 | Evans |
| 2006/0036202 | A1 | 2/2006 | Iwata et al. |
| 2006/0069333 | A1 | 3/2006 | Pidcock |
| 2008/0242957 | A1 | 10/2008 | Gaspard |

OTHER PUBLICATIONS

Acolet et al., "Change in Plasma Cortisol and Catecholamine Concentration Ions in Response to Massage in Preterm Infants", Archives of Disease in Childhood, 1993;68:29-31.

Ottenbacher et al., "The Effectiveness of Tactile Stimulation as a Form of Early Intervention: A Quantitative Evaluation", Developmental and Behavioral Pediatrics, Apr. 1987, vol. 8, No. 2, pp. 68-76.

Mooncey et al., "The Effect of Mother-Infant Skin-to-Skin Contact on Plasma Cortisol and β-endorphin Concentrations in Preterm Newborns", Infant Behavior and Development 20 (4), 1997, pp. 553-557.

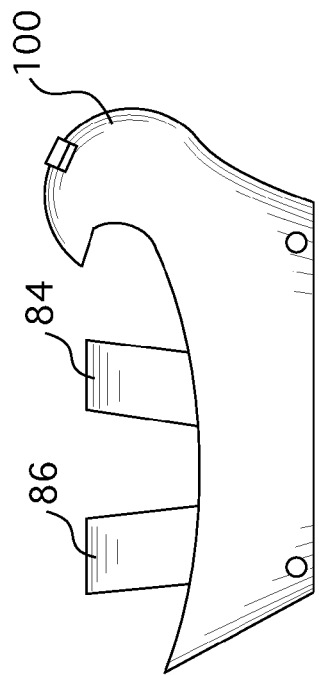
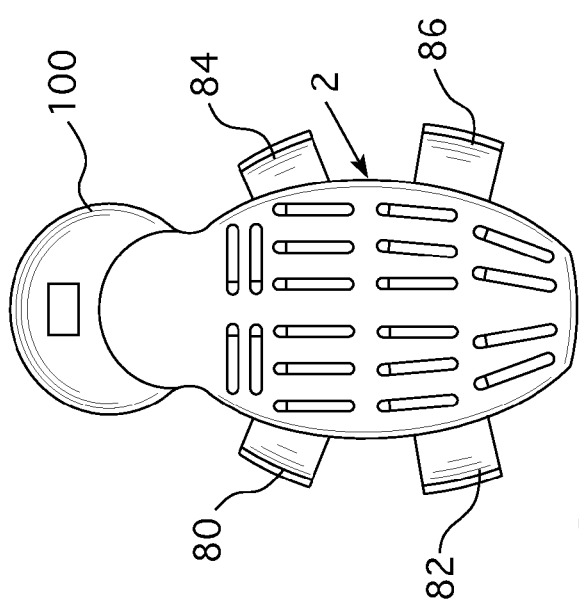
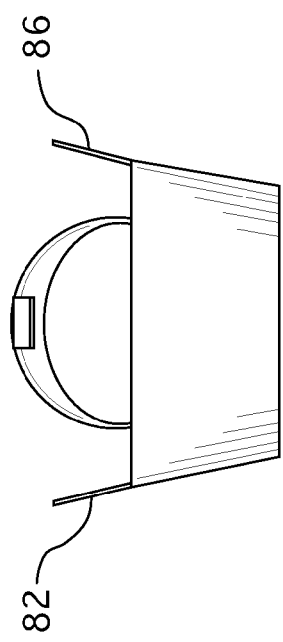

AUTOMATED INFANT MASSAGER

CROSS-REFERENCE TO RELATED APPLICATION

The present application is a continuation-in-part of U.S. patent application Ser. No. 12/051,906, filed Mar. 20, 2008, entitled "Automated Infant Massager," which claims the benefit of U.S. Provisional Patent Application Ser. No. 60/908,749, filed Mar. 29, 2007, entitled "Automated Infant Massager," the disclosures of which are expressly incorporated herein by reference.

BACKGROUND OF THE INVENTION

1. Field of the Invention

The present invention relates to an improved, automated infant massager, and more specifically, it relates to such a massager which is structured to be used on premature infants and can be adapted for use with full-term infants. The invention also relates to such an infant massager which can monitor infant behavioral, physical, and physiological conditions, and in an automated fashion, where appropriate, make adjustments to the massage. Network use of multiple infant massagers is also disclosed.

2. Description of the Prior Art

Hospitals aiming to improve the health status of premature infants must typically separate these babies from their parents at birth in order to administer the necessary medical interventions. Usually isolated in incubators that protect them, these preemies receive significantly less touching than full-term babies in the first days and weeks of life. In fact, many intensive care nurseries have, in the past, discouraged any "unnecessary" touching of neonates, in part because some early reports claimed that certain procedures involving handling, e.g., incubation and diaper changes, led to physiological disruptions, such as decreases in oxygen tension. To some extent, the medical community interpreted these reports as cautions against touching neonates in any other-than-essential manner until the 1987 study at Touch Research Institute ("TRI") by Field et al., Field, T. et al., "Alleviating stress in ICU neonates," Journal of the American Osteopathic Association, 87, 646, 650, (1987), which marked a turning point of premature touch therapy protocol. At TRI, Field et al. documented the effects of touch on forty premature infants. The researchers used a basic infant massage consisting of simple body strokes and passive limb movements for three fifteen-minute periods a day for ten days. The study results showed that the preemies who received massage: (1) averaged a 47 percent greater weight gain, even though the groups did not differ in average food intake (in calories or volume) (which increases their survival rate by 30%); (2) were awake and active a greater percentage of the time and (3) exhibited greater alertness, orientation, and responsiveness on the Brazelton Neonatal Behavior Assessment Scale. Despite the medical benefits of massage, it is time-consuming and requires a trained nurse, which makes its incorporation into the neonatal intensive care unit difficult due to the current nursing shortage, which is estimated to reach about one million by the year 2020.

Other studies have supported these findings and defeated the "common wisdom" about preterm neonates' presumed hyper-responsiveness to touch. Acolet et al., "The effect of mother-infant skin-to-skin contact on plasma cortisol and β-endorphin concentrations in preterm newborns 1," Infant Behavior and Development, Volume 20, Issue 4, pp. 553-55, October-December 1997 discloses, for example, that gentle massage of the head and back of the ICU neonate does not increase the need for oxygen, but in fact, helps the infant cope physiologically with stress. Other studies showed greater weight gain, motor activity and alertness in preterm neonates who did not require intensive care. A meta-analysis by Ottenbacher et al., Oattenbacher K. J. et al., "The Effectiveness of tactile stimulation as a form of early intervention: a quantitative evaluation," Journal of Developmental and Behavioral Pediatrics, 8:68-76, 1987, illustrated that most preterm infants were positively affected by touch stimulation, typically with greater weight gain and better performance on developmental tests. Follow-up research has suggested that massage has long-term benefits for premature infants. Eight months after being massaged in the neonatal ICU, the stimulated babies continued to gain more weight and perform better on developmental tests than a control group.

There are several infant pain and/or distress assessment techniques that clinicians utilize to assess infant, preterm and full term, distress and pain and/or distress level which include the Riley Pain and/or distress Scale, the Neonatal/Infant Pain and/or distress Scale (NIPS), and the Premature Infant Pain and/or distress Profile (PIPP), for example. These assessment techniques are well known to those skilled in the art. They have been validated and shown to be reliable techniques to characterize the pain and/or distress/agitation state of full-term and premature infants. See Duhn et al., "A Systematic Integrative Review of Infant Pain Assessment Tools," Advances in Neonatal Care, Vol. 4, pp. 126-140, June 2004 and P. Hummel et al., "Clinical reliability and validity of the N-PASS: neonatal pain, agitation and sedation scale with prolonged pain," Journal of Perinatology, Vol. 28, pp. 55-60, 2008. These tools provide clinicians with a discrete scale to characterize physiological and behavioral responses of an infant to determine pain and/or distress level. To use these techniques, clinicians rely on their individual expertise to discriminate the infant's physiological and behavioral pain and/or distress responses from other distress responses. There is not apparatus available to clinicians to provide massage or to autonomously characterize pain and/or distress level.

Despite the medical benefits of massage, it is time-consuming and requires a trained nurse, which makes its incorporation into the neonatal intensive care unit difficult.

Another reason why infant massage has not been widely implemented is due to the current nursing shortage, which is estimated to reach about one million by the year 2020.

U.S. Pat. No. 4,088,124 discloses an apparatus said to prevent apnea in a premature infant. This is accomplished by placing an infant on a waterbed and establishing controlled flow of fluid oscillations of the fluid of low amplitude and predetermined frequency under the infant.

Additional prior art patents of general interest are as follows:

| Title | Pat. No. |
| --- | --- |
| Massage Apparatus | 7,322,946 |
| Mechanical Massaging Device | 7,175,592 |
| Massaging Device for Chairs with Guide Rail | 7,004,916 |
| Massaging Bed with Light | 6,814,709 |
| Objective Pain Measurement System and Method | 6,757,558 |
| Physiological Monitor Including an Objective Pain Measurement | 6,751,499 |
| Portable Massager | 6,478,755 |
| Chair Massage | 6,454,731 |
| Cyclically Driven, Straightly and Reciprocally Moving Massage Device | 6,402,709 |
| Portable Vibrating Sleep Pad | 6,175,981 |

-continued

| Title | Pat. No. |
|---|---|
| Massaging Blanket | 6,142,963 |
| Massaging Mattress | 6,052,852 |
| Pulsating Muscle Massaging Device | 5,951,501 |
| Body Contour Massage Device | 5,820,573 |
| Therapeutic Treatments Machine | 5,505,691 |
| Personal Cuddling & Massaging Device | 5,125,399 |
| Sleeping Inducing Devices | 5,063,912 |
| Massage Machine | 5,054,472 |
| Apparatus for Massaging the Body by Cyclic Pressure & Constituent | 5,052,377 |
| Electrochemical Massage Apparatus | 4,834,075 |
| Punctual Massager Using Vertical Rotary Movements of Massaging Pins | 4,777,945 |
| Treatment of Colic Infants | 4,754,747 |
| Method & Apparatus for Therapeutic Motion and Sound Treatments of Infants | 4,681,096 |
| Method for Treating Premature Infants | 4,088,124 |
| Massage Device | 3,994,290 |

SUMMARY OF THE INVENTION

The present invention has met the above-described need by providing an automated infant massager which is suitable for use with premature infants, as well as full-term infants. The massager provides a base for supporting the infant and a plurality of first movable massage elements structured to underlie a portion of the infant with at least one motor for effecting reciprocating movement of the plurality of first movable massage elements for massaging the back. The massager also may have a plurality of second movable massager elements for massaging the infant's arms. A head support may be provided for the infant with a plurality of third movable massage elements massaging the infant's head, and a plurality of fourth movable elements may be provided for massaging the infant's shoulders. Various combinations of movable elements may be provided for effecting automated reciprocating massage to various parts of the infant's body. For example, the plurality of first movable massage elements may be employed to massage a portion of the back of the infant's legs in addition to the infant's back.

In one embodiment of the present invention, an automated infant massager system has at least one automated infant massager with a plurality of massage elements structured to underlie at least a portion of the infant and a processor for receiving infant information directly or indirectly from the infant massager and a network system. The infant information includes information relating to at least one of the physical, behavioral, or physiological responses of the infant, and infant identification information. Sensors and other monitoring accessories provide electronic, visual, and audible feedback information regarding various characteristics of the infant.

The automated infant massager system may include, in one embodiment, a plurality of automated infant massagers functioning in a network environment.

It is an object of the present invention to provide an automated infant massager which is suitable for massaging a premature infant, as well as full-term infants.

It is a further object of the present invention to provide such a massager which may be remotely controlled through a handheld transmitter, for example, or may have direct controls on the massager itself or both.

It is a further object of the present invention to provide such an infant massager which is provided with efficient controls to establish the desired functionality and safety while effectively massaging the infant and to provide direct or remote alarm indicators in the event of a malfunction or infant safety indicators.

It is a further object of the present invention to provide such an automated infant massager which provides monitoring of automated infant massaging and adjustment of the massage characteristics, such as duration and intensity, where feedback indicates such action is desirable.

It is a further object of the present invention to provide such a structure which is provided to monitor physical, behavioral, and physiological characteristics of the infant being massaged.

It is a further object of the present invention to employ such a structure which enables the use of a plurality of such automated infant massagers as part of a network system to facilitate monitoring of more than one infant simultaneously.

It is a further object of the present invention to employ such a structure which enables the use of a plurality of such automated infant massagers as part of a network system used by a plurality of users simultaneously.

These and other objects of the present invention will be more fully understood from the following detailed description of the invention and reference to the illustrations appended hereto.

BRIEF DESCRIPTION OF THE DRAWINGS

FIG. 1(a) is a detailed plan view of a portion of the track and massaging elements which move thereon.

FIG. 4 is a top plan view of the infant massager of FIG. 3 in the open position.

FIG. 5 is a front elevational view of the infant massager of the present invention in the open position.

FIG. 6 is a right elevational view of the infant massager of the present invention in the open position.

DESCRIPTION OF THE PREFERRED EMBODIMENTS

As employed herein, the terms "behavior" and "behavioral state" mean actions or reactions indicative of the agitation state of the infant including, but not limited to, reactions to external stimuli and shall expressly include sleeping, consolability state, crying, frowning, smiling, and facial grimacing.

As employed herein, the term "physical" means any actions or reactions to external stimulus expressly including, but not limited to, movement of the limbs, the entire body, fingers, and toes, brow movement, squirming, mouth tensing, eye squeezing, brown bulge, and nasolabial furrow.

As employed herein, the term "physiological" means any information, action or reaction pertaining to the physic and/or the internal system of the body including reactions to external stimuli, including, but not limited to, heart rate, breathing rate, brain activity, hormone levels, blood pressure, oxygenation saturation level, gestation age, and birth age.

As employed herein, "safety" relates to: a) any mechanical software or technical operations that are within the desired/specified design margins for the operation of the massager and b) an appropriate physiological, physical, and behavioral response from the infant to the stimulus of the massage which indicates that the infant is not at increased risk for decreasing health or physical harm such, but not limited to, an abnormal heart rate, and/or abnormal respiration.

The infant massager will contain a housing unit that will massage the head, back, arms, shoulders, and legs of the infant through a plurality of massage elements. The device will not massage the chest or directly on the infant's spinal column. Each side of the device will have two protrusions that will be used to massage the top surface of the arms and legs. The support surface of the device will be lined with soft materials and boundaries for the infant where needed.

Figure 1:
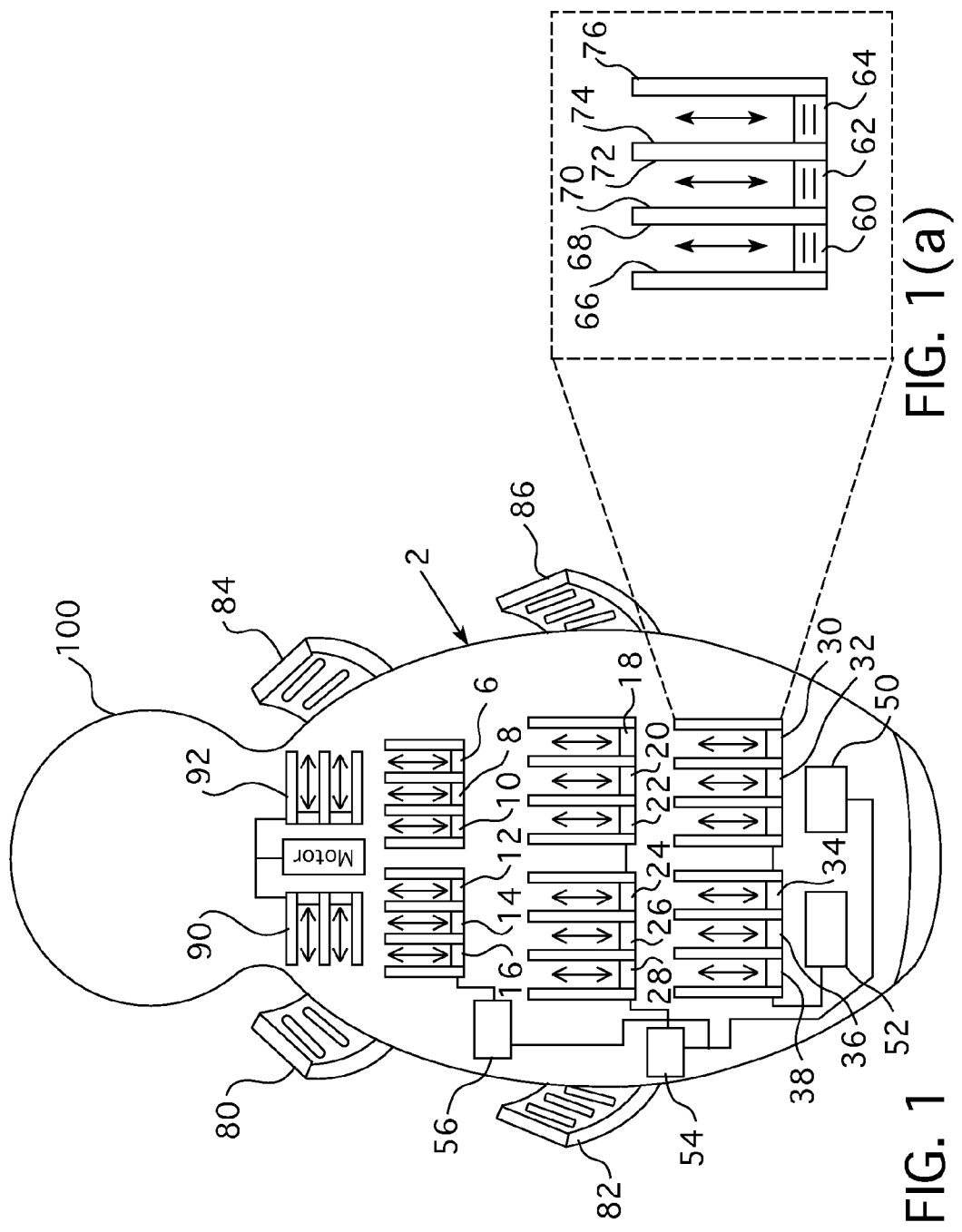
FIG. 1 is a schematic, top plan view of a form of automated infant massager of the present invention.

Referring to FIGS. 1 and 1(a), there is shown an automated infant massager which has a base 2, a plurality of first movable massage elements, such as 6, 8, 10, 12, 14, 16, 18, 20, 22, 24, 26, 28, 30, 32, 34, 36, 38, which in the form shown, are structured to partially support and massage the back of an infant by moving in the reciprocal direction shown by the arrows, which in the form shown, will extend in a direction generally parallel to the infant's spinal column. In the form shown, a battery 50 will serve to energize at least one motor 52. In the specific form shown, motors 54, 56 are operatively associated with the first plurality of massage elements 6-38 (even numbers only). Alternatively, if desired, the massager may be plugged into an electrical outlet and energized in that manner. The transmissions may be of any desired means which, as well known to those skilled in the art, will convert the output of a motor shaft into reciprocating movement of the first plurality of movable massaging elements 6-38 (even numbers only). As shown in FIG. 1(a), movable massage elements 60, 62, 64 are each operatively associated with a pair of parallel tracks, such as (a) 60 and tracks 66, 68; (b) movable massage element 62, with tracks 70, 72; and (c) movable massage element 64 being associated with generally parallel tracks 74, 76. At the lateral sides of the base 2 are a plurality of second massage elements secured on supports 80, 82, 84, 86.

Figure 2:
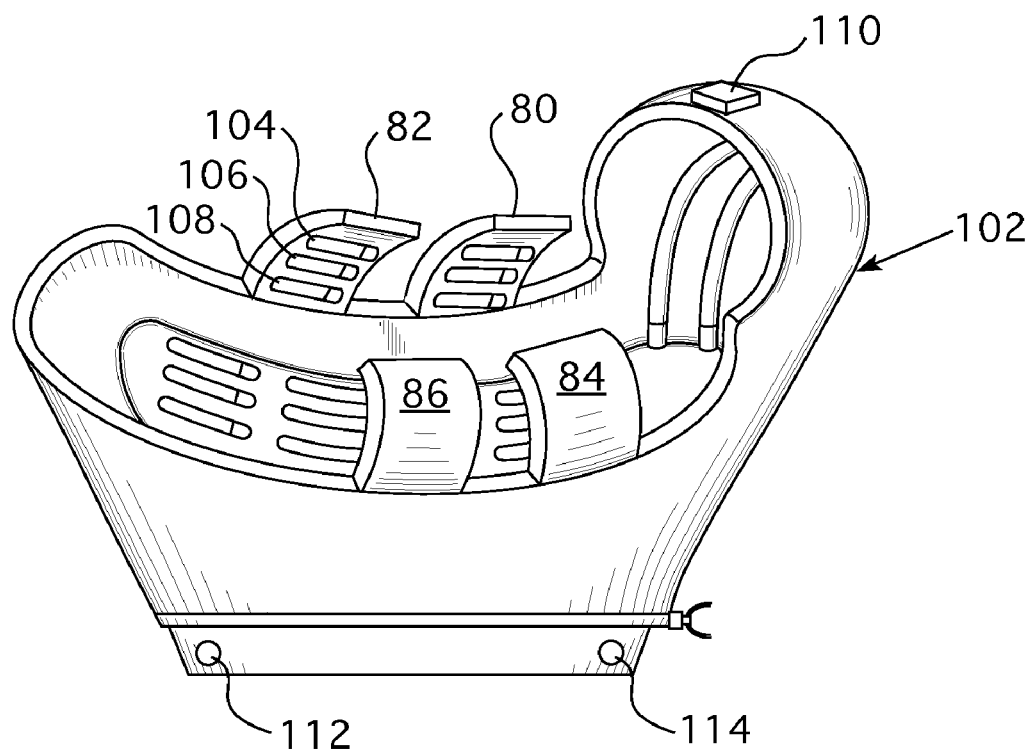
FIG. 2 is a perspective view of a form of the infant massager of the present invention with a cover in place.

FIG. 2 shows the infant massage apparatus of FIG. 1 with the supports 80, 82, 84, 86 in the open position. These each support the plurality of second movable massage elements which will massage portions of the arms and legs of the infant. See, for example, elements 104, 106, 108 of support 82. The boundaries 85 (FIG. 3) preferably will be soft, so as to provide a soft barrier to help keep the infant in position. It also serves to surround the infant to provide boundaries and help the infant feel secure. It also shows the brow monitor 110 which is structured to embrace the head of the infant and indicate the movement of the infant's the brow and eye movement when the brow monitor is placed in contact with the infant's forehead. FIG. 2 also shows the brow monitor 110 which is in the storage position on top of the cover 102. In use, it is secured to the forehead of the infant by a mild adhesive and serves to provide an indication of the infant wrinkling its brow or eye wincing, which is a known sign of pain or other discomfort. This information will be delivered to the massager's microprocessor to aid in the determination of the infant's pain or distress level. The brow monitor 110 also serves to monitor head movement of the infant. Depending upon the type of movement that is being sensed by the brow monitor 110 in a particular instant, the information wirelessly transmitted to the remote unit could trigger an alarm message or merely signal that the infant has moved out of position such that the head is no longer contacting the monitor. It will be appreciated that the prime function of the brow monitor 110 is to monitor brow movement, blinks, and facial movements to provide meaningful feedback.

Massage unit cover 102 has a plurality of openings through which movable massage elements, such as 104, 106, 108, will pass. FIG. 2 also shows the power input jack connection 112 and monitor jack input 114 for visually monitoring the performance of the system.

Figure 3:
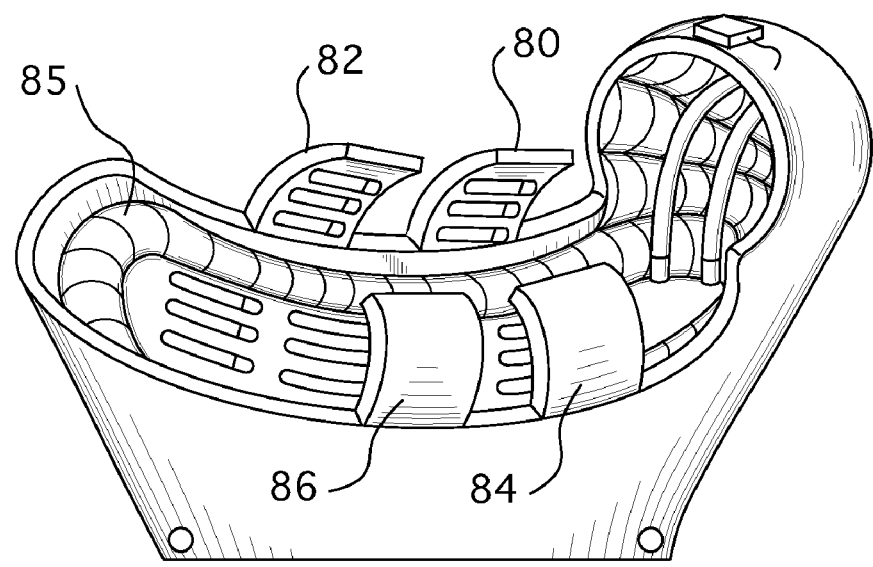
FIG. 3 is a form of infant massager of the present invention with the massager shown in the open position.

FIG. 3 shows the massaging apparatus in the closed position with the boundaries 85 serving to provide padded protection around the circumference of the upwardly-open recess which receives the infant.

FIGS. 4 through 6 show, respectively, plan front elevational and right-side elevational views of the massaging device in the open position for use with premature infants.

Figure 9:
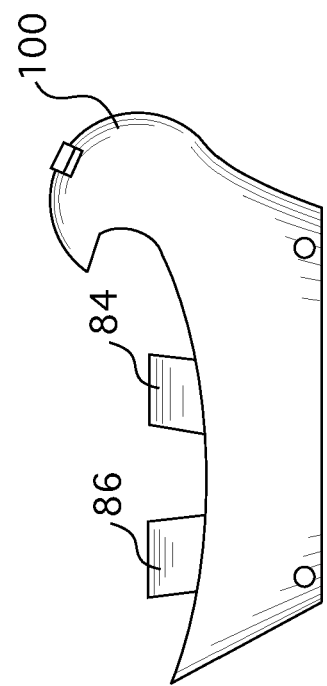
FIG. 9 is a right-side elevational view of the massager of FIG. 8.
Figure 7:
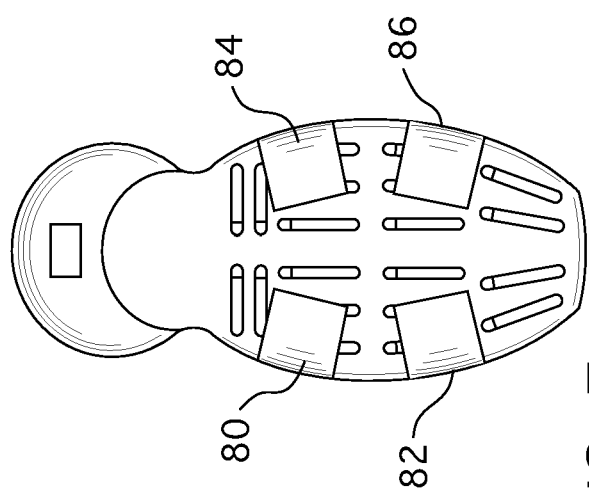
FIG. 7 is a top plan view of the infant massager of FIGS. 4-6 in the closed position.
Figure 8:
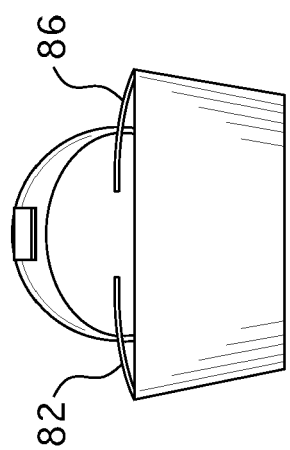
FIG. 8 is a front elevational view of the infant massager of FIG. 7.

FIGS. 7 through 9 show the massaging device of FIGS. 4 through 6 in the closed position.

Figure 10:
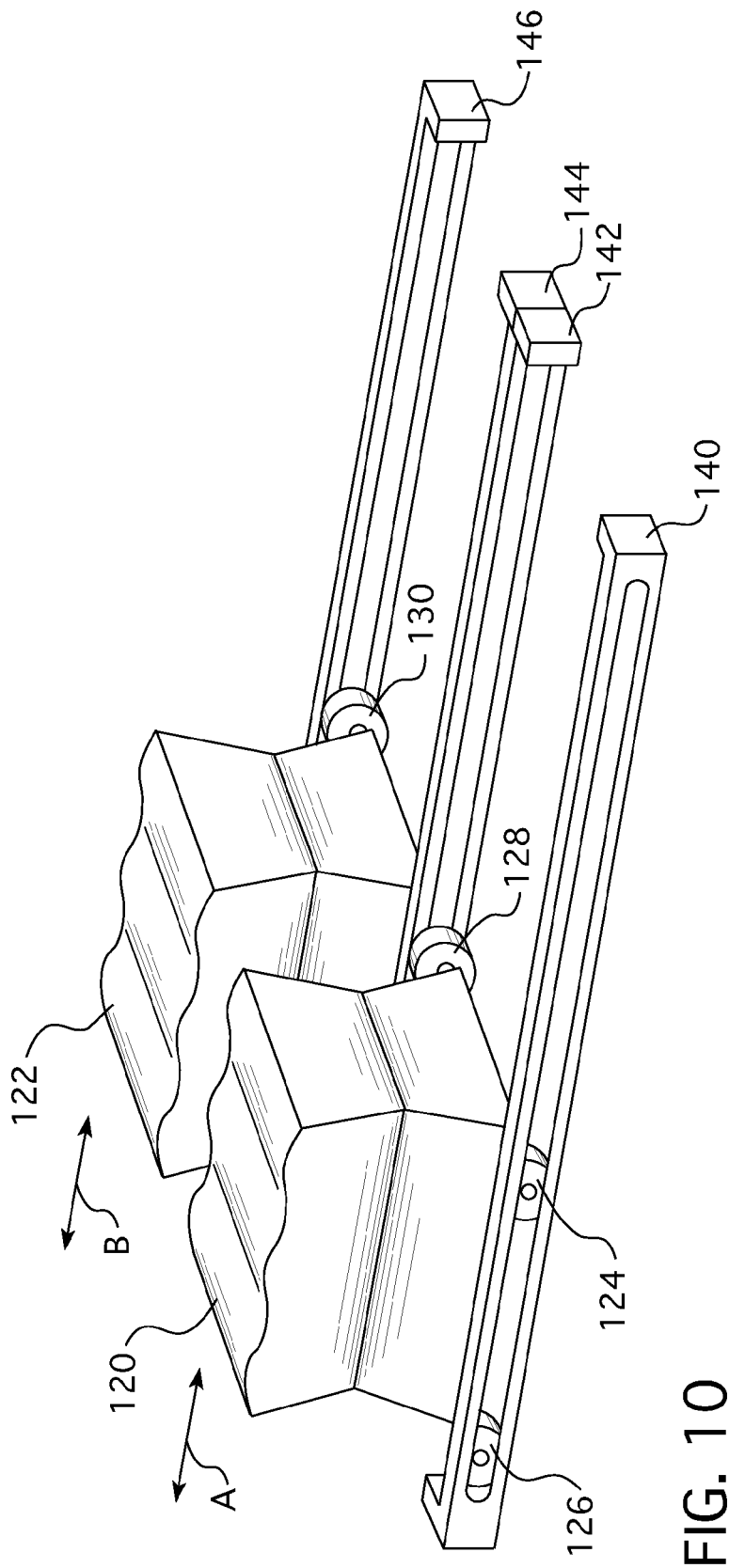
FIG. 10 is a schematic illustration of two massaging elements the and associated tracks.

FIG. 10 schematically illustrates a first massaging element 120 and a second massaging element 122 each being on four wheels 124, 126, 128 with the fourth wheel of massaging element 120 not being shown and with solely wheel 130 of massaging element 122 being shown. They are confined by a plurality of tracks 140, 142, 144, 146 and reciprocate in the indicated movement directions (Arrows A and B). It is noted that the upper surfaces of massaging elements 120, 122 are irregular and undulate so as to permit efficient massaging movement as the massaging element moves along the patient in paths parallel to each other.

Figure 11:
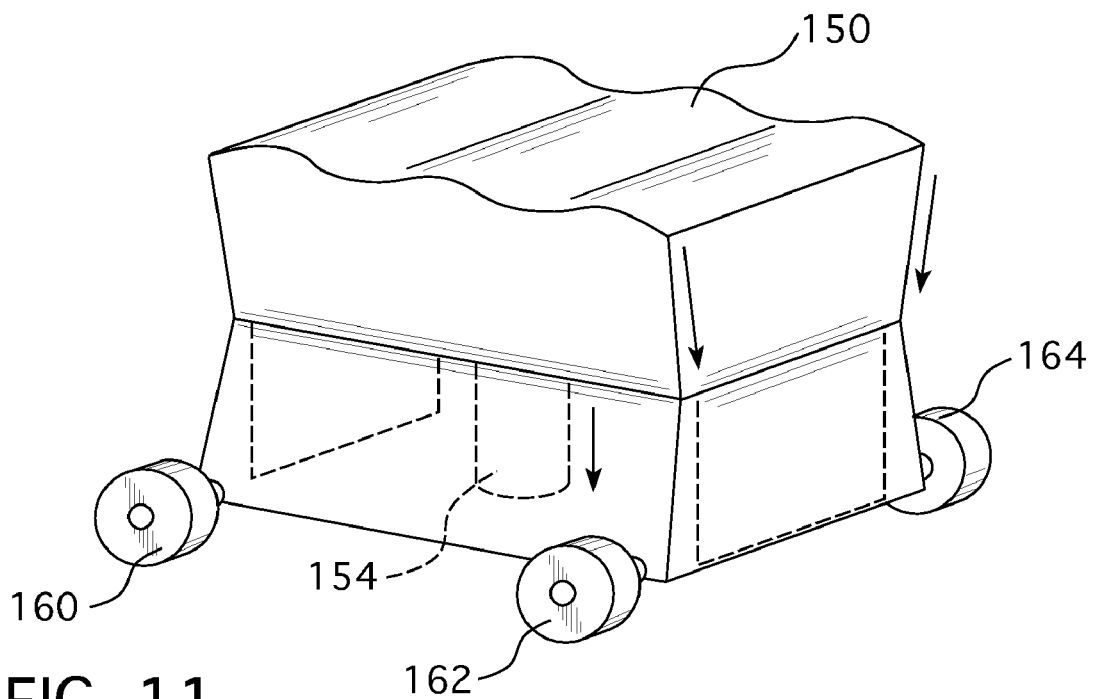
FIGS. 11 and 12 show in perspective, respectively, a massaging element of the present invention in the expanded and contracted positions.
Figure 12:
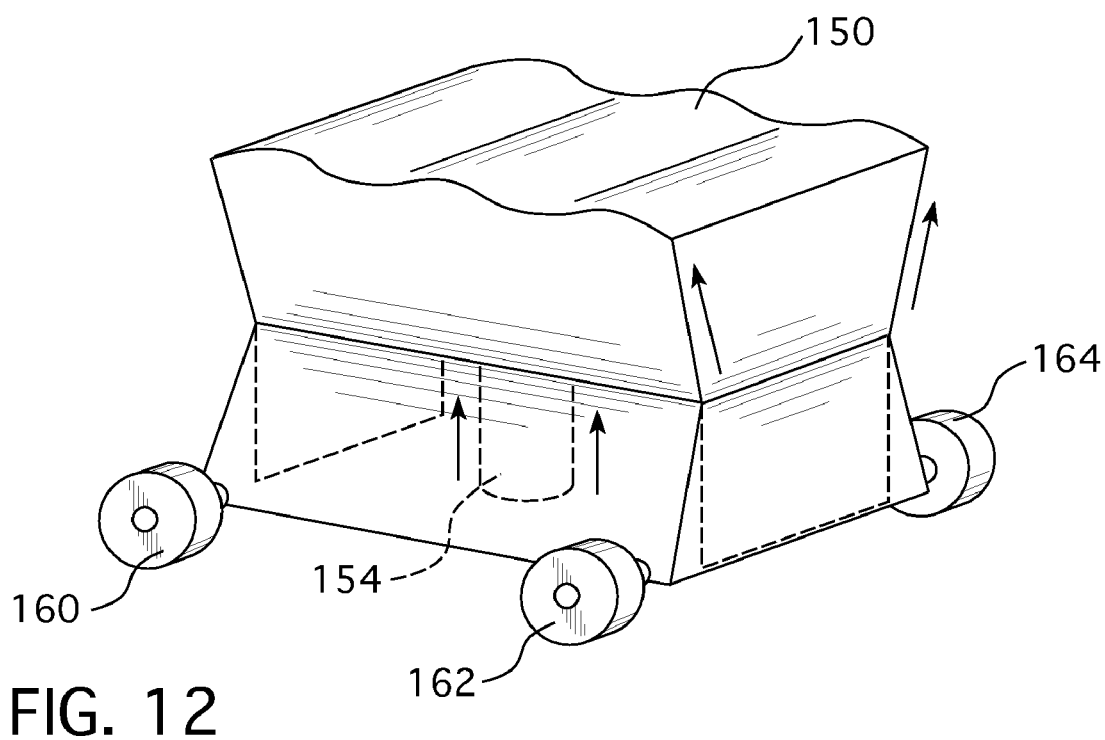

FIGS. 11 and 12 show, respectively, a massaging element in an extended position and in a contracted position. This permits variations in the intensity of the massage. This may be accomplished by any desired means, such as a rod or a piston 154 axially reciprocating in a vertical direction while engaged with the undersurface of the upper portion 150. It will be appreciated that the two pairs of wheels 160, 162, 164 (only three shown in FIGS. 11 and 12) may be restrained for the desired reciprocating movement by having upwardly-open grooves in the upper portions of tracks 140, 142, 144, 146 of FIG. 10. It will be appreciated that the reciprocating motion of the massaging elements may be achieved in a number of different fashions known to those skilled in the art.

Figure 13:
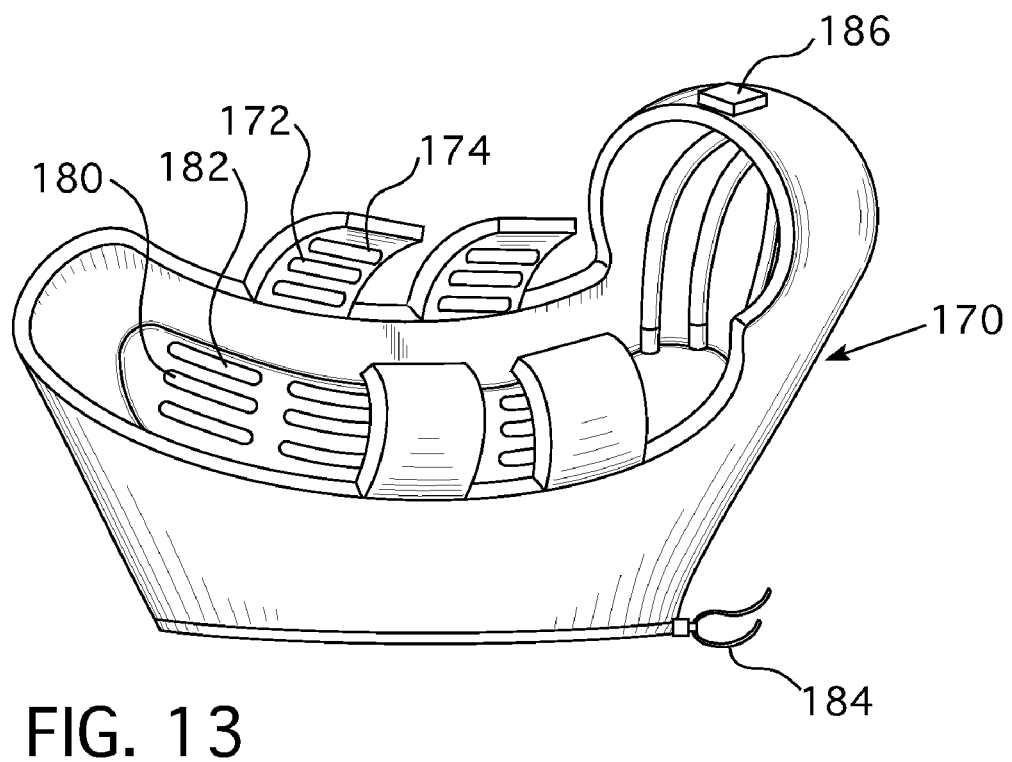
FIG. 13 is a form of cover for the infant massager of the present invention.

FIG. 13 shows a disposable cover 170 for the infant massager, which in each location, has slots, such as 172, 174, 180, 182, for passage of the individual massaging elements therethrough. An opening 186 for the brow monitor is provided. A tightening device, such as a tie string 184, may be provided to secure the cover to the massaging element.

Figure 13A:
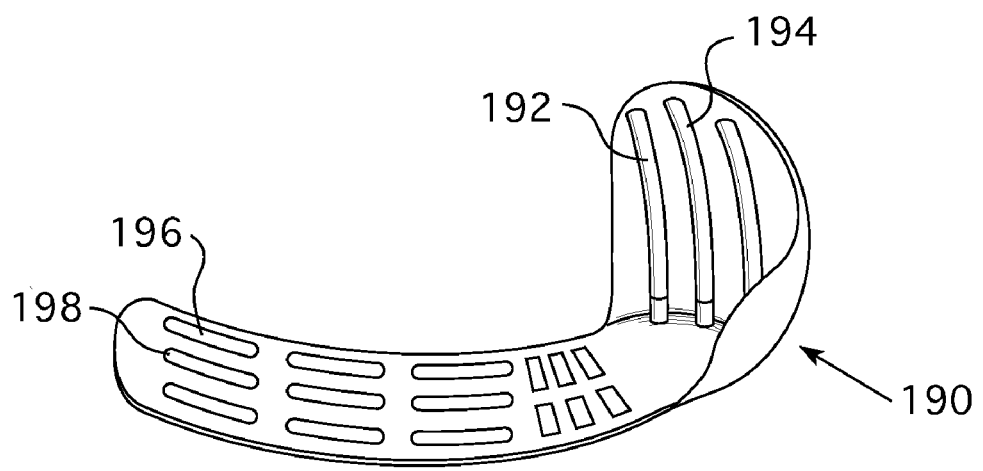
FIG. 13(a) is an alternate form of cover for the infant massager of the present invention.

FIG. 13(a) shows an alternate form of cover 190 which has a plurality of openings, such as 192, 194, 196, 198, for passage of the massaging elements therethrough.

Figure 14:
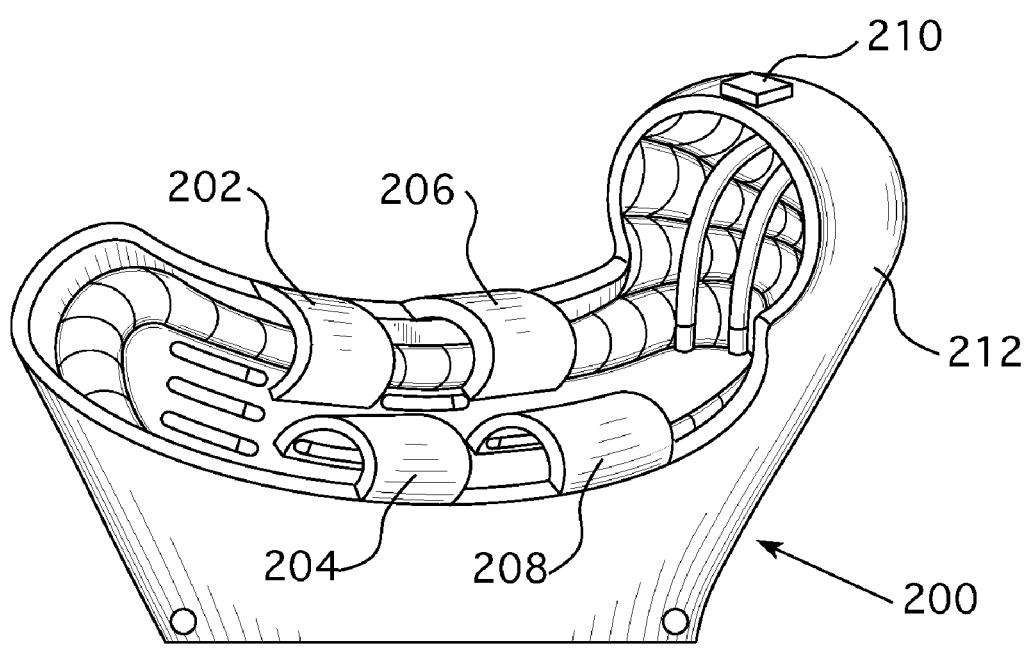
FIG. 14 is a perspective view of the infant massager of the present invention in the closed position.

FIG. 14 shows a perspective view of the infant massager 200 in the closed position with the arrays of leg massagers 202, 204 bent inward and an array of arm massagers 206, 208 folded inward. The brow monitor 210 is secured to the head support 212, as there is no infant in the device.

Figure 16:
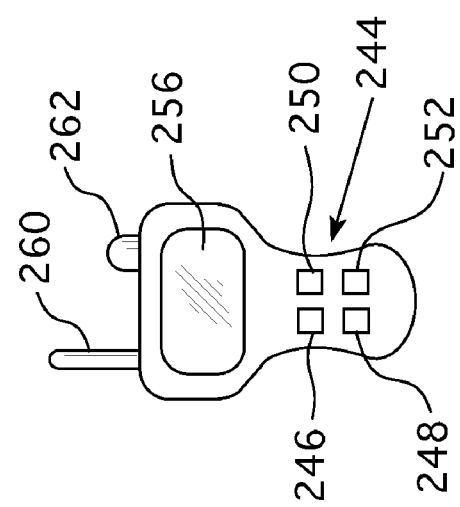
FIG. 16 is a view of a remote transmitter for controlling certain functions of operation of the massager in FIG. 15.
Figure 15:
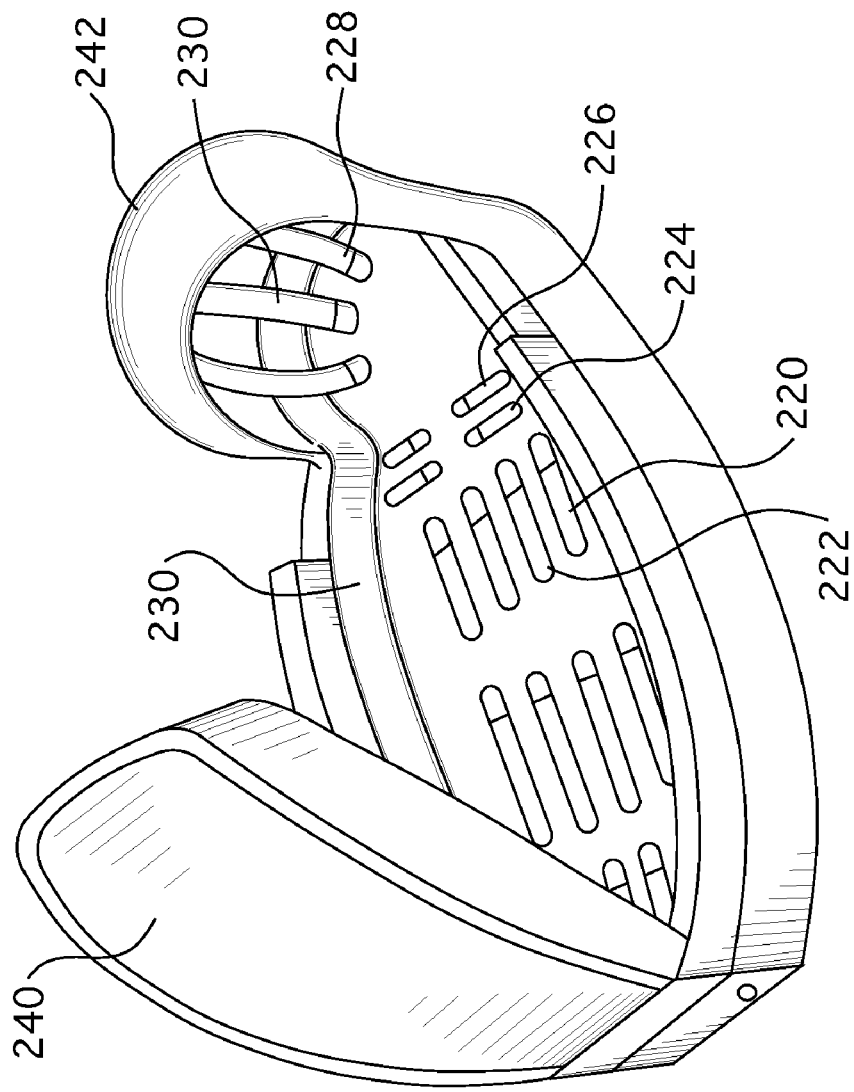
FIG. 15 is a perspective view of an alternate embodiment of a massager of the present invention for use with full-term infants.

Referring to FIGS. 15 and 16, there is shown a version of the infant massager which has the arrays of movable massage elements, such as 220, 222, 224, 226, 228, 230, for example, and a padded border 230 around the interior, so as to protect the infant. In addition, there is a hinged rotatable cover 240, which is structured to be in an up position as shown in FIG. 15, and in a lower position covering the feet and legs of the infant with gentle pressure.

The exterior of the massaging unit will contain outlet/input slots for connecting other accessories and monitoring devices.

FIG. 16 shows a remote wireless controller 244 which is structured to have two-way communication with a transmitter (not shown) operatively associated with and preferably secured to the infant massager. The controller has a plurality of control buttons 246, 248, 250, 252, a display window for displaying data, facilitating control messages, and transmitting of the same. The display window 256 can also be structured to view the infant in real time when desired. An antenna 260 is integrally formed and projects from the remote receiver transmitter. A light 262 is structured to illuminate either in solid form or flashing form when an alarm condition exists or other attention-giving messages are desired. The remote receiver transmitter 244 can serve to turn the massage unit on, turn it off, program the transmitter operatively associated and preferably physically attached to the infant massager as to cycles of operation, and coordinate the receipt of emergency messages, such as undesired shutdown. It will be appreciated that while four control buttons 246, 248, 250, 252 are shown in FIG. 16, any number of desired control buttons may be employed.

The massaging unit will adjust the massage based on feedback from the internal monitoring sensors/equipment.

Figure 18:
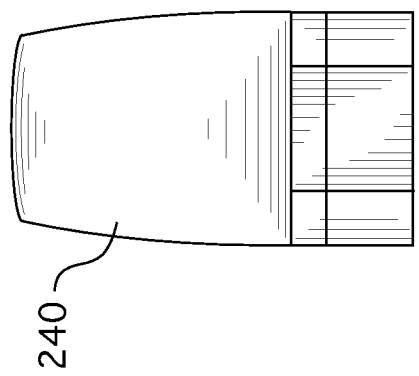
FIG. 18 is a front elevational view of the massager of FIG. 17.
Figure 19:
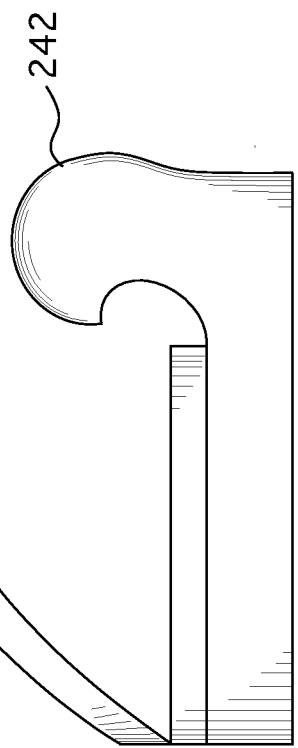
FIG. 19 is a right-side elevational view of the infant massager of FIG. 17.
Figure 17:
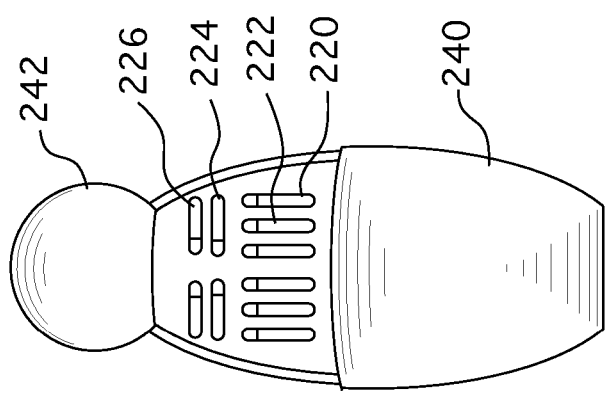
FIG. 17 is a top plan view of a full-term infant form of infant massager of the present invention.

FIGS. 17 through 19 show, respectively, a top view, front elevational view, and right-side elevational view of the massage unit of FIG. 15 with the cover 240, head support 242, and arrays of massaging elements 220, 222, 224, 226, for example.

Figure 20:
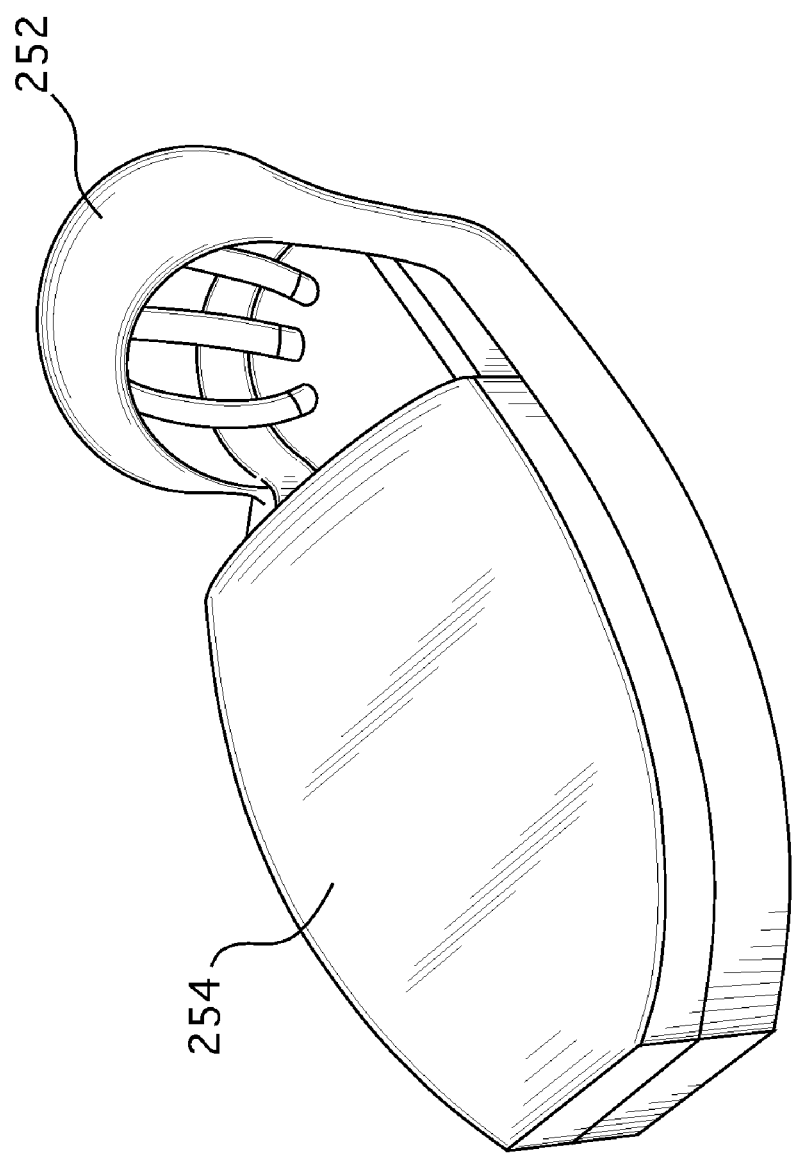
FIG. 20 is a perspective view of the closed-position massager of FIGS. 17 through 19.

FIG. 20 shows a unit having an adjustable head support 252 and an adjustable top cover 254 which is structured to cover the infant's chest, legs, and arms. If desired, a cover/insert 190 (FIG. 13(a)) serves to provide a boundary between the infant's skin and the massaging platform/massager. The cover/insert 190 will be placed inside the massager before the infant is placed inside the massager. The cover/insert is preferably made of a biocompatible disposable material. The cover 254 may have slits or other openings to receive the massage elements therethrough. In the alternative, the cover 254 may be structured without such slits in order that the pressure or force from the massage elements is delivered to the infant through the thickness of the cover 254, the infant support platform, and cover/insert 190. As will be known to those skilled in the art, the cover may be secured to the massager by any appropriate means, such as elastic hooks, Velcro material, pressure-sensitive adhesive surfaces, and the like. The infant massager will include a method of measuring the force applied during the massage, temperature of the infant, the movement of the infant, behavioral and physical changes of the infant to the massage, the audio from the infant during the massage, and video images of the infant. The means for monitoring these characteristics will be known by those skilled in the art. These monitoring sensors may be formed integrally with the massager or be separated therefrom but be operatively associated therewith. This monitoring will facilitate determinations of the infant's distress and pain level, as well as allowing determination of the physical characteristics of the infant, such as weight. They will also permit measurement of the applied force and the applied pressure. This information will be part of what is provided to the processor 402 (FIG. 31) for the feedback loop.

In another embodiment of the present invention, a source of auditory output which may deliver soothing sounds to the infant may be provided. For example, such sounds could be that of soothing music, ocean sounds, or heartbeat sounds. Similarly, a visual system for getting the infant's attention in order to sooth and calm could be operatively associated with the massager. If desired, one may provide, within the infant's line of sight, objects which may serve to stimulate the infant manually in a noncontacting fashion, such as mobiles, mirrors, toys, and the like.

These visual features could be provided by a mirror or a mobile attachment to the massager in a position which can be viewed by the infant.

The infant support platform of the infant massager may be rigid and have a firm platform surface upon which a soft bed will be placed on top of to evenly distribute the weight of the infant and to provide a soft boundary between the platform and the infant. The insert 190 will then be placed on top of the mattress. Along the inside border of the massager, a soft lining may be placed to provide a soft boundary to protect the infant. The preferred embodiment of the bed would be a gel mattress or isotonic foam enclosed in soft cloth. The mattress may have openings/slits to allow the massage elements and their covers to pass through and enable the reciprocating movement of the massage elements so that the massage can be administered to the infant. The mattress and the lining could be detachable or non-detachable from the massaging base unit. The mattress may, if desired, contain an indentation or crevice to receive the infant's body in the massager. The indentation/crevice may have the general contour of infant's body to provide additional boundaries to maintain the infant's position and to indicate to the user where the infant should be place in the massager.

The remote receiver transmitter 244 (FIG. 16), 420 (FIG. 31) will be provided with a display screen, as well as data entry and control buttons. The display screen will provide the user with output received from the massager or associated accessories to provide information employable in determining by the processor 42 or by the user 422 whether a change in the massage program is desirable. Among the features provided on the remote receiver transmitter 244, 420 may be a manual on/off switch, controls to effects the settings for the massage, such as duration and intensity, a scanner to decode information from an RFID tag or a bar code, entry information regarding the specific infant, and, along with two-way communications, enablement between the remote receiver transmitter 244, 420 and the massager.

Figure 21:
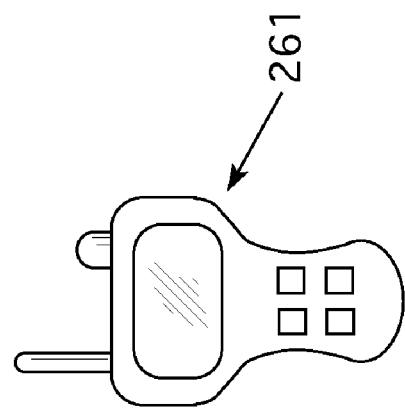
FIG. 21 is a remote wireless transmitter for controlling the operation of the infant massager of the present invention.

The automated infant massager and the remote receiver transmitter 244, 420 will contain a processor and supporting hardware and software to control and coordinate the overall operations and functions of the infant massager and the remote receiver transmitter, respectively. The processor for the massager will employ the necessary software and hardware to receive, analyze, interpret, monitor, and transmit signals necessary to coordinate the proper and safe operation of the massager, initiate the alarms, communicate with the wireless remote controller and/or central receiver/transmitter, and communicate with the user. The processor and supporting software within the massager will be used to interpret, monitor, and adjust the settings of the massager, which include, but are not limited to, settings associated with the sensors, mechanical system, electrical, and audio system. The processors will be powered to the power source associated with the massager. The massager may contain one or more processors or microcontroller processor. The massager may also have the technology to non-invasively monitor and measure brain activity to determine the distress state of the infant using optical means, such as near infrared spectroscopy or EMG. An alternate embodiment of the exterior automated infant massager cover would have an insert 190 that is placed inside the massager that is not fitted to cover the whole massage unit. An associated remote receiver transmitter 260 is shown in FIG. 21.

The massaging device can be used in an incubator, a radiant warmer, or on a table. The massaging device massages premature infants to help improve their health and help them gain weight. A disposable cover design 170 (FIG. 13) that closely fits the geometry of the premature infant massager is provided to maintain the sterility of the massager.

The massaging device may integrate with neonatal intensive care unit ("NICU") monitoring equipment and an electronic medical record system/network. The massaging device may automatically adjust the intensity of the massage based on an internal feedback system that relies on the behavioral and physical response input from the infant. The massaging device may automatically shut off for potential safety problems or negative feedback from the infant.

In one embodiment, a disposable cover should be made of a soft, flexible material 170, 190. The disposable cover should be a very soft material that does not irritate the infant's skin.

Figure 23:
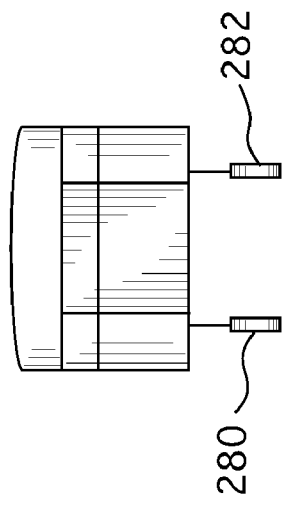
FIG. 23 is a front elevational view of the infant massager of FIG. 22.
Figure 24:
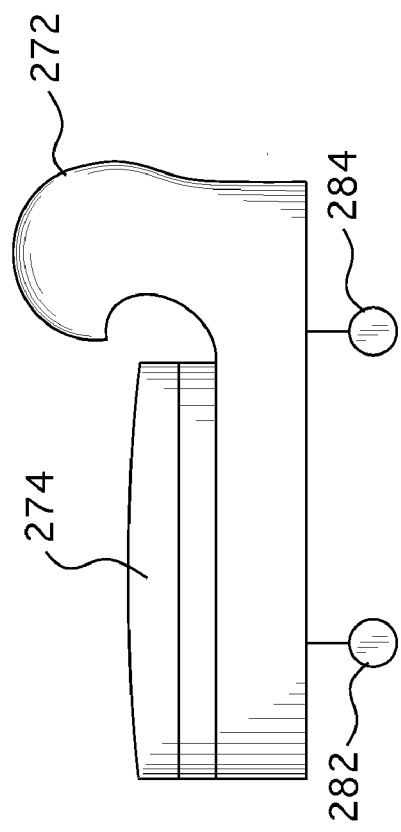
FIG. 24 is a right-side elevational view of the infant massager of FIG. 22.
Figure 22:
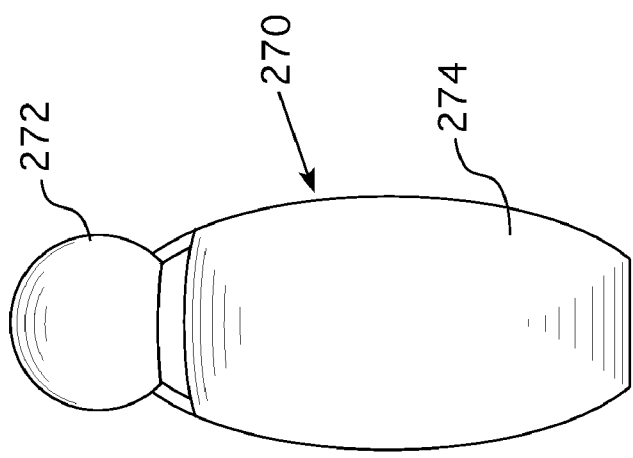
FIG. 22 is a top plan view of a form of infant massager of the present invention.

The embodiments of FIGS. 22 through 24 show, respectively, a top plan view of an infant massager 270 having a head support 272 and a cover 274 with four depending wheels 280, 282, 284 (only three are shown) to facilitate movement of the unit for use by a full term or premature infant.

The control mechanism associated with the massaging device and massage adjustment/features could be placed on the massaging unit.

The massaging device may also be accompanied by a user's kit. The kit will contain all accessories needed to facilitate and/or enhance the massage. It will also contain any directions to set up the massaging system and the infant for the massage.

Examples of items the kit could contain: (a) the disposable cover; (b) brow monitor (similar to an infant forehead thermometer except it detects displacement); (c) massage oil and (d) connection to the vital signs monitor.

For full-term infants, a massaging kit would contain massage oil and a disposable cover.

The infant support surface should be made out of any materials that meet the user requirements, such as metal or plastic, for example. It should be able to facilitate being wiped and sterilized.

The massaging elements should be made hard and strong. These could be made out of appropriate materials that meet the requirements of the device. They should be covered by a flexible, wipeable material. It should be able to facilitate being wiped and sterilized.

The track/pulley/conveyor belt system could be made of a material that is strong, yet lightweight.

Figure 25:
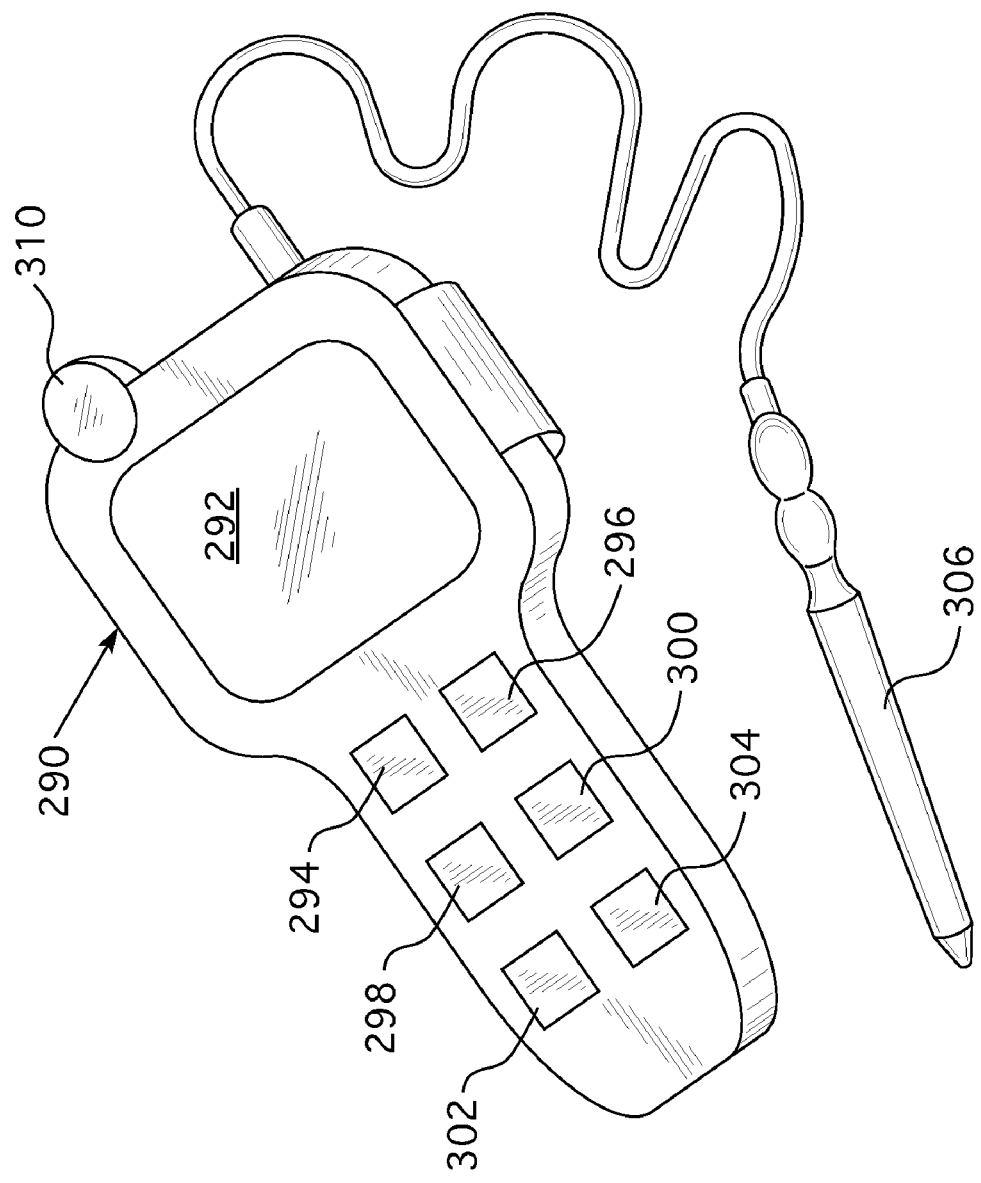
FIG. 25 is a perspective view of a form of remote receiver transmitter employable with an infant massager of the present invention with the pointer pen in the operating position.
Figure 26:
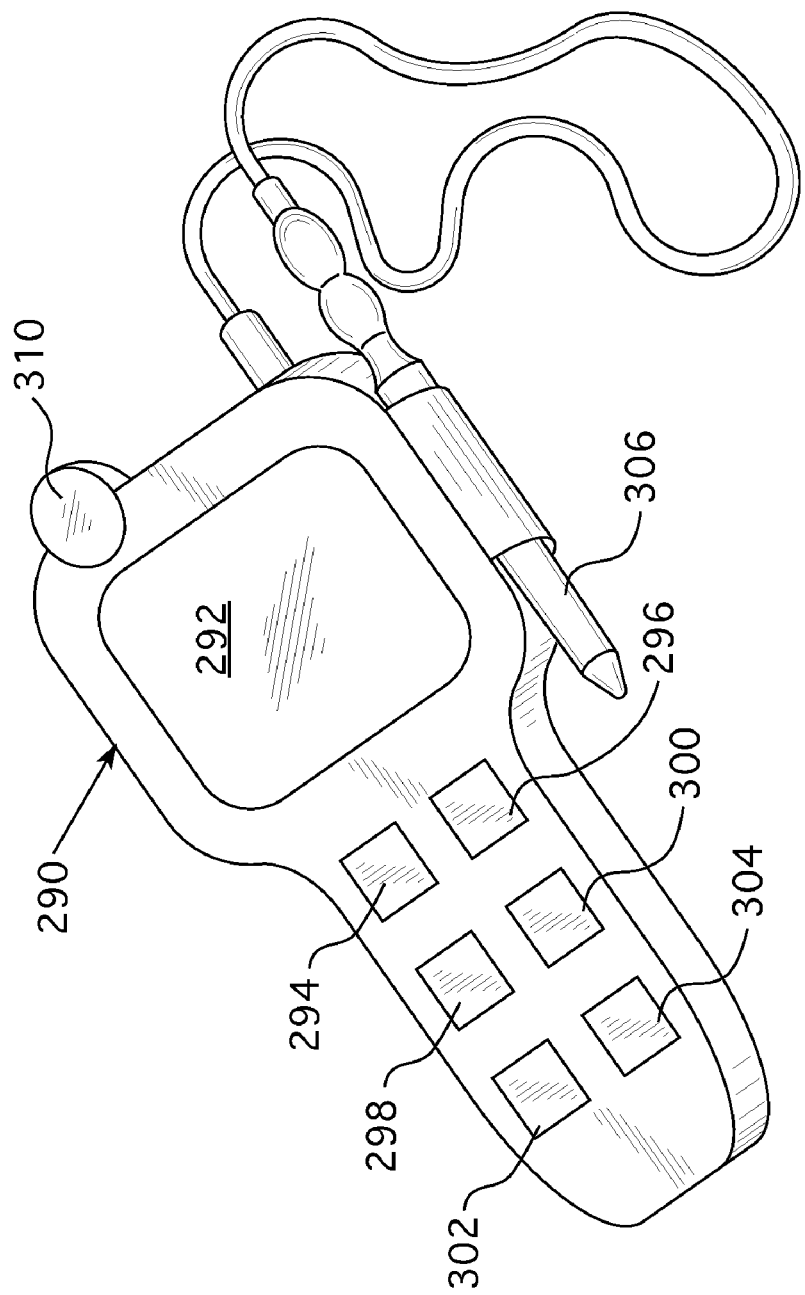
FIG. 26 is a perspective view of a form of transmitter for operating the infant massager with the pointer pen in the storage position.

FIGS. 25 and 26 illustrate a remote receiver transmitter or base station 290 having a display screen 292, control buttons 294, 296 for on/off controls, and additional controls 298, 300, 302, 304 with a pointer pen 306. A light 310 is provided and may be illuminated in a continuous manner or blinking form and may be used as an emergency alarm indicator. Also, a speaker (not shown) may be provided to deliver an audible alarm. It may be secured to and operatively associated with the infant massager may be provided thereon, as well as on the remote receiver transmitter. The remote receiver transmitter or base station 290 is structured to have wireless communication with a receiver transmitter operatively associated with and preferably on the massager unit. The remote receiver transmitter 290 may also contain a bar code or RFID scanner (not shown) operatively associated with the remote receiver transmitter 290 to allow the infant's identification tag to be scanned to enter partial patient/infant information into the massager.

The remote receiver transmitter 290 for the infant massager allows the user to both receive and input information about the massager and the infant. This may include: (i) notifying the user of "power off" through sounds, lights, or vibrations, (ii) monitoring of power supply, (iii) allowing a user to manually stop and start the device, (iv) allowing the user to select intensity of massage, (v) optimizing/coordinating the usage of the device among the premature infants in a NICU unit, (vi) allowing the user to select the monitored physical parameters of the infant, (vii) allowing the user to get a printed summary of the infant's behavior and vitals changes at the end of the massage, (viii) alerting the user to when the device needs to be recharged, and (ix) alerting/informing the user about any safety problem or mechanical failures. It may also allow the user to enter information about the infant by scanning the infant's identification bar code or RFID tag. The massager may adjust the massage based on feedback from internal and external monitoring equipment.

The massaging device for infants can be aimed at monitoring and/or improving overall developmental skills, sleep, colic, apnea, and overall health and health status of the infant. The massaging device will adjust the massage based on behavioral state, physical, and physiological feedback. The massaging device will preferably massage the front and back of the body including the arms, legs, back (not along the spinal column), and head. The massaging device also includes features to enhance sleeping and comfort. The massaging device can provide video of the infant being massaged to the clinician The massage device may contain safety features that cause the device to turn off automatically.

The automated infant massager will contain a remote receiver transmitter that may:

(a) allow the user to adjust the massage setting;
(b) allow the user to view video of the infant during the massage;
(c) contain mechanisms to alert users when the device has stopped;
(d) contain mechanisms to alert the user to mechanical problems/failures;
(e) collect identifying information from a bar code or RFID tag; and
(f) allow the user to manually stop or start the massage.

The massager device preferably has a lid/top cover 240 (FIGS. 17-19), 254 (FIG. 20), 274 (FIGS. 22 and 24) that has adjustable height features.

The massage device maintains massaging elements in contact with the body and adjust the massage to maintain appropriate pressure.

Figure 27:
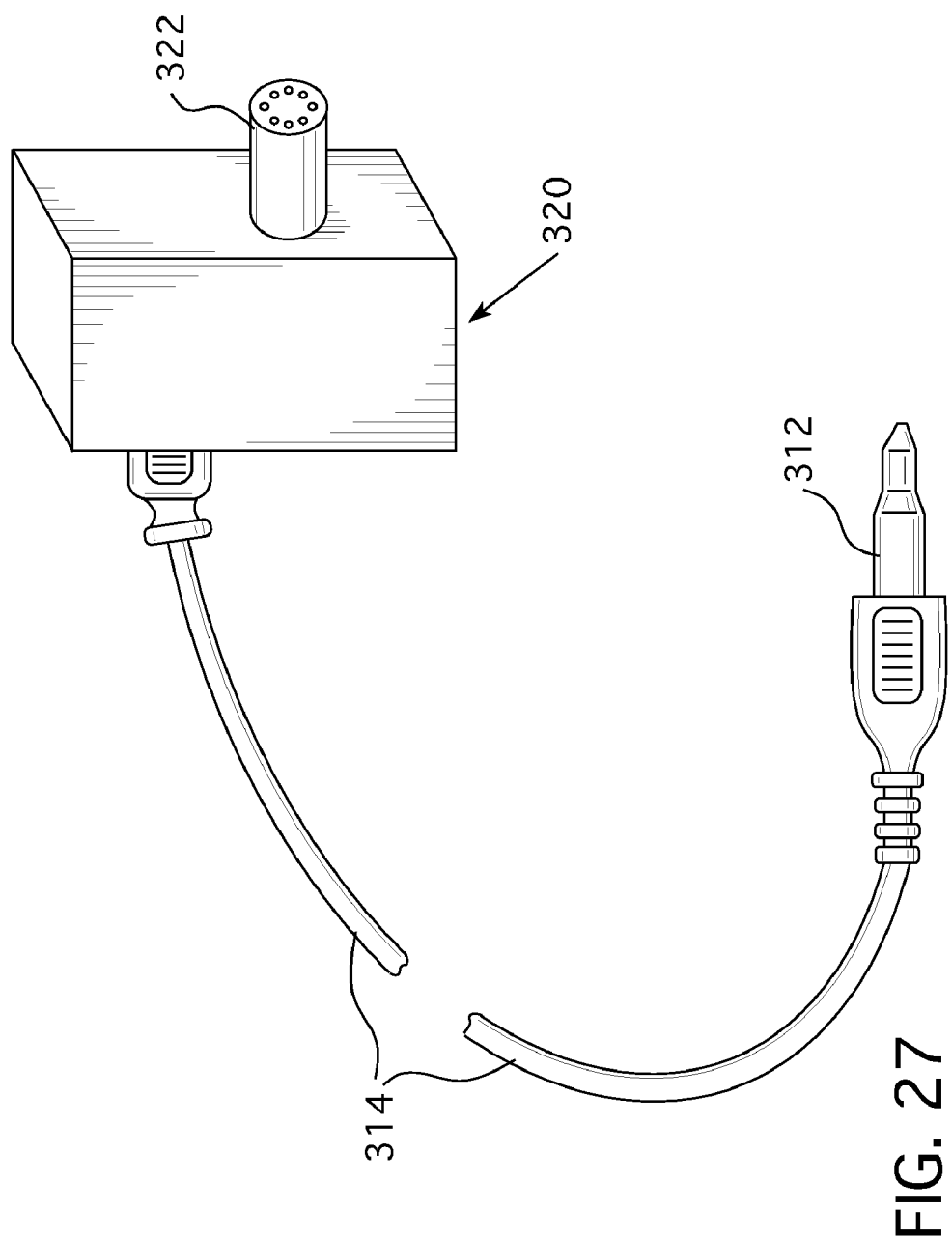
FIG. 27 is a schematic view of an accessory for monitoring cardio-respiration of the infant.

FIG. 27 illustrates an example of a jack 312 which plugs into the infant massager, and by a suitable electrical lead 314, is connected to the massager and is operatively associated with a microprocessor, which is part of the massager. This will allow the massager to physically interface with the hospital's data network and system for data transmission/retrieval. The jack could also be used to facilitate the monitoring of the infant's cardio output and respiratory rate via an cardio-respiratory monitor external to the massager. The connection 322 connects the automated massager to the hospital system for data transmission and/or retrieval or to an external cardio respiratory monitor to collect information which will be sent to the microprocessor unit 320 with the input/output passing over lead 314 through the jack 312 to the microprocessor for further analysis.

Figure 28:
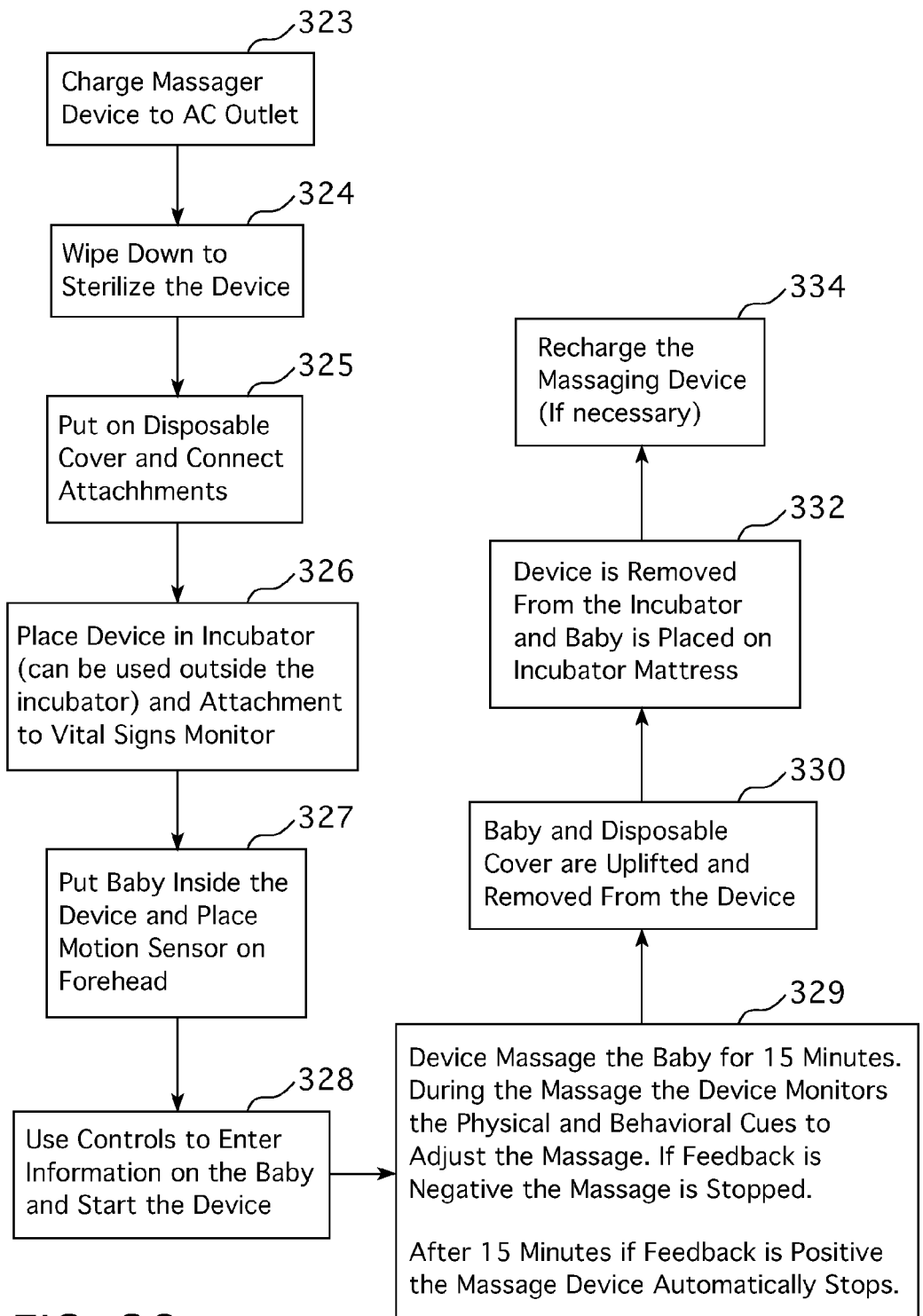
FIG. 28 is a flow diagram showing operation of an infant massager of the present invention on a premature infant.
Figure 29:
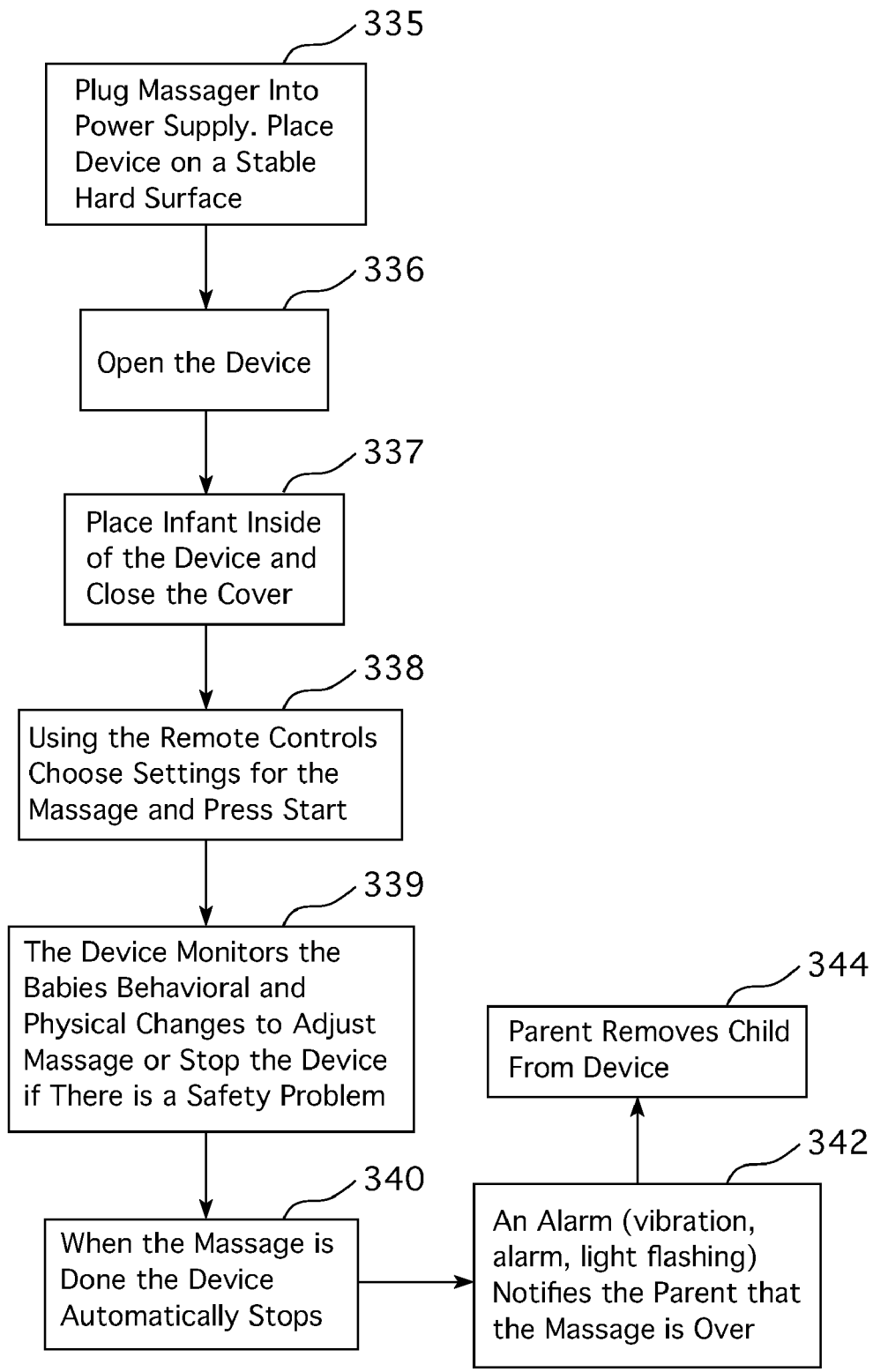
FIG. 29 is a schematic view showing a sequence of operation of an infant massager for full-term infants.

FIGS. 28 and 29 illustrate, in a block diagram, a sequence of operation, respectively, for premature infants and full-term infants. Referring in greater detail to FIG. 28 and the use of the system for premature infants, the unit is first charged in an AC outlet 323 and is then wiped down to sterilize the device 324. A disposable cover/insert in placed into/over the massager and the attachments are then connected/placed in position 325. The device is placed in an incubator or can be employed outside the incubator or attached to a vital signs monitor 326. (This is not the preferred embodiment. In the preferred embodiment the massager will have its own inherent cardio respiratory monitor.) The infant is then placed inside the device, and a motion sensor is placed on the forehead 327. The infant may then be connected to the cardio respiratory monitor. Controls, including the scanner, are employed to enter information on the infant and start the device 328. The device massages an infant for fifteen minutes, and during the massage, the device monitors the physical, physiological, and behavioral state changes through a feedback loop in order to adjust the massage. If the feedback is inappropriate, the massage is adjusted or stopped. After fifteen minutes, if the feedback is appropriate, the massage device automatically stops 329. The infant and the disposable cover are lifted and removed from the device 330 after which the device is removed from the incubator, and the infant is placed on the incubator mattress 332. The massaging device is then recharged if it is in need of such charging 334.

Referring to FIG. 29, use of the massager on a full-term infant is considered. The massager is first plugged into a power supply and placed on a stable, hard surface 335 after which the device is opened 336. The infant is placed inside the device and connected to the monitoring sensors, and the cover is closed 337. Employing remote receiver transmitters, settings for the massage are established, and the start button is pressed 338. The device monitors the infant's behavior and physical changes to adjust the massage or stop the device if there is a safety problem 339 after which when the massage is completed, the device stops automatically 340. An alarm, which may be a vibration, an audible alarm, and/or a flashing light, notifies the user that the massage is over 342 after which the user removes the infant from the device 344.

The massaging unit for a full-term infant contains a housing which, preferably, massages all parts of the body except for the spinal column. The housing unit for the massage device will have a cover that will secure the infant in the device. The cover/lid 240, 254 of the device is attached to an adjustable support which will allow the lid 240 to be lowered into contact with the infant's skin. The unit will preferably also include an infant support surface where the infant will be placed. The support surface will be covered with soft materials and will have boundaries where needed.

The massaging elements of the device will protrude from open slots on the support surface 220, 222, 224, 226 and from the underside of the lid 240, 254 (FIG. 17) of the massaging device. The slots for the massaging elements may be arranged in parallel, horizontal, and/or vertical rows 220, 222, 224, 226. The massaging elements may be enclosed by a thin, flexible, expandable material.

The massaging elements may consist of a rectangle-shaped piece with a modulated/wavy top surface (the surface that comes in contact with the skin) 120,122 (FIG. 10). The massaging element will be secured to a track system 140,142, 144, 146 or a similar system known to those skilled in the art. The massaging elements will move in reciprocating movements sequentially by body part. All massaging elements located in the same region of the body will move in the same reciprocating movement simultaneously.

It will be appreciated that various means well-known to those skilled in the art can be employed to effect the desired reciprocating movement of the massage elements. For example, a linear actuator of the electro-mechanical variety may be employed with the linear movement from the output of a single motor employed to reciprocate a single massage element or a plurality of elements. Alternatively, rack and pinion means may be employed with the rack being secured to the underside of a massage element and the pinion engaged therewith driven in rotary fashion by the output shaft of the motor with or without an intervening speed adjusting gear box. Another approach would be to have the massage elements secured to a conveyor.

Figure 30:
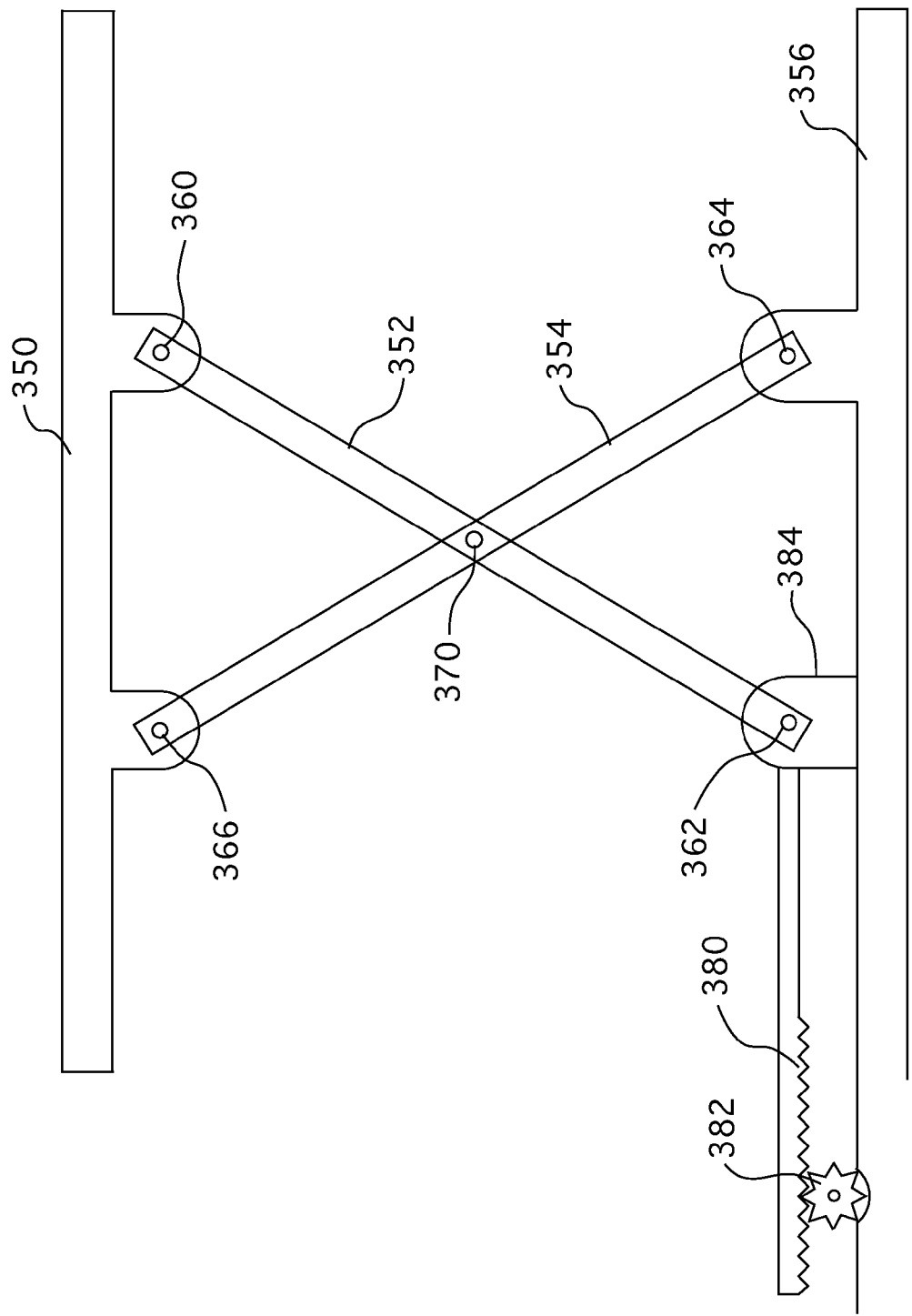
FIG. 30 is a schematic view of apparatus usable to raise and lower a massage element.

Referring to FIG. 30, there is shown a way of elevating and lowering the level of the upper portion of a massaging element. The upper platform 350, which will support the massaging element upper part, has pivotal linkage to links 352, 354. Link 354 pivots about pivots 364, 366, the former of which is connected to base 356. Link 352 pivots about 360, 362 with pivot 370 serving to connect pivotally the two links 352, 354. Rack 380 is secured to element 384 which is slidably secured to base 356. Output of the motor (not shown) functions to rotate pinion 382 which is engaged with rack 380. It will be appreciated that rotation of pinion 380 causes lateral movement to the right or left of rack 380 and responsive movement to linkage of platform 350 upwardly or downwardly through the responsive movement of 384., thereby adjusting the height of the massage element.

The massaging elements 6, 90, 92, 104, 106, etc. of the device will preferably protrude from open slots on the infant support surface and from the under-surface of the arm and leg massage protrusion. The slots for the massaging elements will be arranged in parallel, horizontal, and/or vertical rows. The massaging elements may be enclosed by a thin, expandable material which will isolate them from the outside environment. In the alternative, the infant support of the massager may be made of durable, resilient material which preferably is cleanable and which can be sterilized or cleaned through an appropriate solution and wiping down.

The inside of the housing unit will contain a rechargeable battery which could be used to power the motors needed to move the track or conveyor belt, the track or conveyor belt system, and the massaging elements. The exterior of the massaging unit will contain outlet/input slots to connect an external vital signs monitor or other monitoring and soothing accessories to the device.

It will be appreciated that the reciprocating massaging elements are secured to the infant massager in such a way as to resist separation, but permit the desired reciprocating movement.

While the preferred approach of having several groupings of pluralities of reciprocating massaging elements has been shown, it will be appreciated that variations in the number and orientation of such elements may be employed if desired.

In a preferred approach to the invention, as illustrated, an upwardly open recess for receipt of an infant will be provided. Particularly with respect to premature infants, it is preferred that the contour of the massager be curved so as to create a generally concave, upwardly facing configuration to facilitate the infant being held in such a position.

Among additional features, which can be provided in the massager are:

(a) can be used in an incubator, a radiant warmer, or on a table;

(b) massages premature infants to help improve their health and help them gain weight;

(c) having a disposable cover design closely fits the geometry of the premature infant massager to maintain the sterility of the massager;

(d) integrates into the NICU monitoring equipment;

(e) automatically adjusts the intensity of the massage based on a feedback system that relies on the behavioral and physical responses input; and (f) automatic shut off for potential safety problems or negative feedback from the infant.

While, for simplicity of disclosure, the remote receiver transmitter has been shown as a wireless unit, it may, if desired, be connected to the massager through a wired connection. The system will have at least one microprocessor for receiving information from the massage unit and delivering information thereto and the remote receiver transmitter. The remote receiver transmitter may function as a base station. The microprocessor may be a separate unit or may be part of the remote receiver transmitter or part of a separate base station. Among the functions of the microprocessor will be the receipt of information from the receiver transmitter of the massager, process the same, and send control signals to the remote receiver transmitter, which in turn, will send signals to the receiver transmitter. The microprocessor may also receive and process information from a cardio-respiration monitor which is monitoring the infant.

Example

An example of operation of the massager will be considered. Before using the device, it should be charged by plugging into a wall outlet or directly powered by plugging it into a wall outlet. The massager will then be wiped down with a disinfecting cloth to clean the massaging surface. The disposable cover/insert will be fitted to the massager with the arms and legs massagers in the open position (see FIG. 1). A small forehead motion sensor will be connected to the device. The device will be placed inside the incubator (or on table surface). The infant will be placed inside the massager, and the infant massager's cardio respiratory monitor will be connected to the infant. The forehead motion sensor will be placed on the infant's skin over the brow. The user will then use the handheld control unit system to:

(a) enter the infant's name, gestational age, and weight;

(b) choose the intensity of the massage;

(c) choose the length of the massage, such as five or ten minutes, for example; and (d) start the massage.

The device will preferably not start until information on gestational age and weight has been entered. The massager will continuously monitor the infant once activated to adjust the massage or turn off the device if the infant is showing signs of distress.

Once the settings have been chosen, the device will be activated to move the arms and legs massager elements, which are in the open position, and slowly curl them down until the massager elements are in light contact with the infant's skin. All massaging parts will adjust as necessary to administer the specified intensity of massage based on the infant's weight, gestational age, and the initial measured behavioral, physiological and physical response.

The device will start by massaging the infant in the following sequence massaging each area for roughly one minute (total time of five minutes):

(a) head;

(b) upper shoulders and arms;

(c) back (from upper shoulders to lower back);

(d) arms (from shoulders to wrist); and (e) legs (upper thighs to ankle).

The massager will rest for three minutes between massaging sessions. If a ten-minute massage session has been chosen, two five-minute massages will be given. If a fifteen-minute massage session has been chosen, three five-minute massage sessions will be administered with two three-minute breaks between sessions. During the massage session, the nurse will be able to use either a network control system or a handheld control system to monitor the infant's response to the massage by pressing infant response button. When the massage is completed, the massager will automatically turn off. An alarm on the handheld control system will sound an alarm, vibrate, and blink a flashing light (a blue light for an example) to inform the nurse that the device has been turned off. If the device automatically shuts off for any reason other than the completion of a massaging session, a different light color (a red light, for example) will flash along simultaneously with the vibrations to alert the nurse to any possible problems with the infant or the device.

Figure 31:
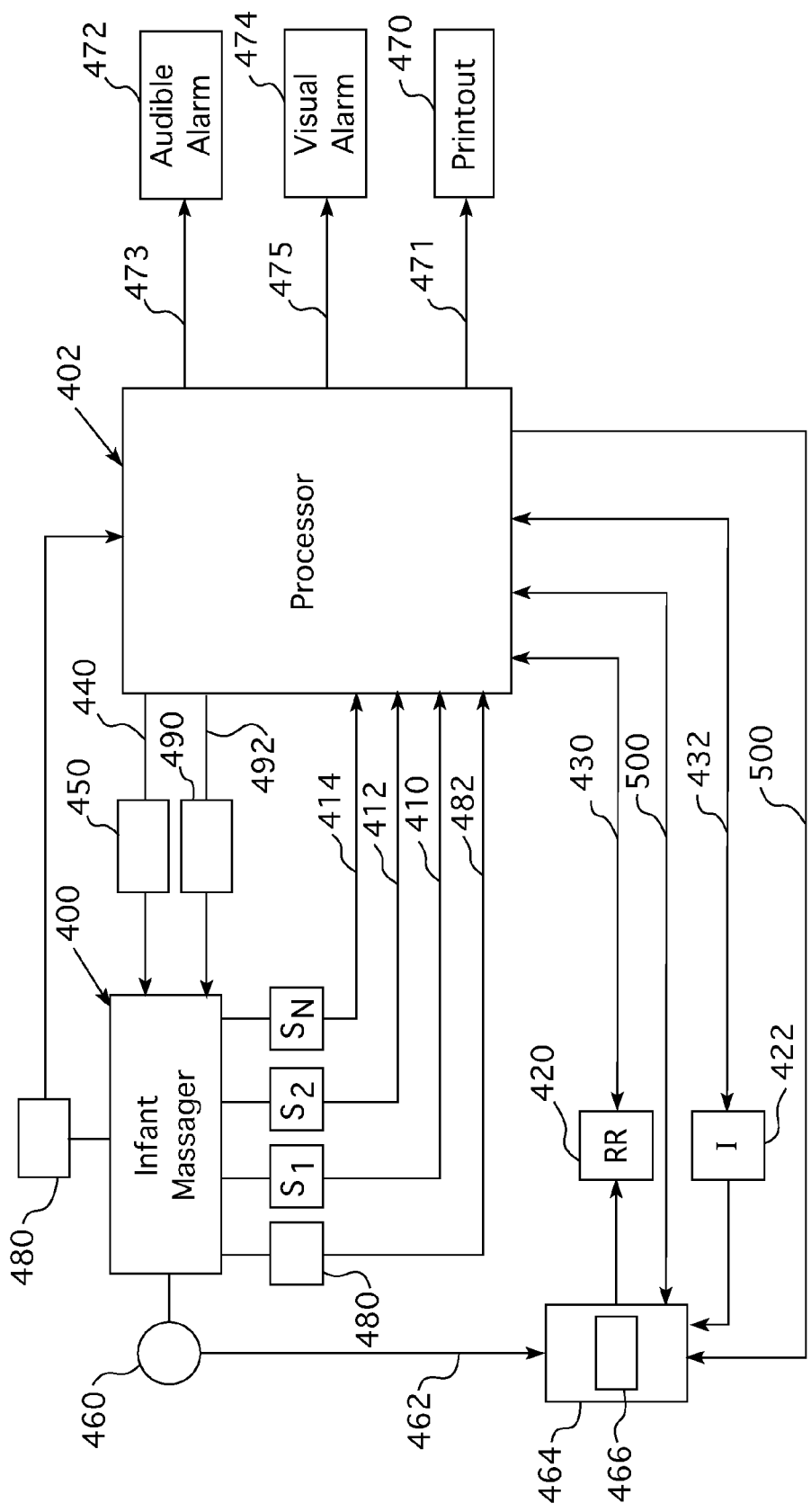
FIG. 31 is a flow diagram indicating one preferred sequence of operation of the massager of the present invention.

Referring to FIG. 31 in greater detail, it is seen that the automated infant massager 400 is operatively associated with processor 402, which contains the desired software and stored data to facilitate efficient functioning of the massager in a manner to be disclosed hereinafter. Considered in its broader aspects, a plurality of sensors $S^1$, $S^2$ through $S^N$ are operatively associated with the infant massager and by lines 410, 412, 414, respectively, provide input to the processor 402 responsive to information received through their respective sensing operations with respect to infant massager 400. Lines 410, 412, 414 may be hard-wired connections, or in the alternative, may involve wireless communication. The processor 402 may also receive additional input from remote receiver transmitter RR 420 and user input I 422 with lines 430, 432 facilitating communication in both directions between the remote receiver transmitter RR 420 and user input I 422 over lines 430, 432, respectively, which may be hard-wired or wireless connections. Based upon the input which is received and the stored data, the operational software contained within processor 402 may issue over line 440 one or more control signals through controller 450 to the massager 440. For example, the information received from sensors $S^1$, $S^2$, $S^N$ will be compared with the desired values for such sensor signals, and in the event that the operation of the massager and the condition of the infant are as desired, no corrective control signal needs to be emitted by the processor 402 over line 440 which may be a hard-wired or wireless connection. On the other hand, if there is a departure from the desired values of information received from sensors $S^1$, $S^2$, $S^N$, the processor 402 may issue a corrective control signal over line 440, which may involve, for example, a change in intensity of the massage, as by moving the massage elements to a different elevation, as hereinbefore disclosed, or may involve shutting down the massage unit or may involve an adjustment of the time cycle for which the automated infant massager 400 was to operate or termination of the massage cycle. Referring to FIG. 31, the system may provide an audio pickup 480 for receiving sounds emerging from said infant and through line 482, or in the alternative, wireless connection, delivering the same to the remote receiver transmitter RR 420 on the processor 402.

A further feature of the present invention provides a processor 402 being structured to provide audio transmission to the infant through speaker 490. This transmission may assume a wide variety of forms, such as soothing music, the voice of the infant's parents, ocean sounds, or heartbeat sounds, with a view toward enhancing the infant's relaxed state.

In addition to receiving information from sensors from $S^1$, $S^2$ through $S^N$, the processor may receive information from a user through a remote receiver transmitter RR 420 or by direct input I 422 from the user. Such input from either source may involve a change in the status of the automated infant massager 400, such as, for example, alteration of intensity or duration of the massage or shutting down operation of the massager 400. Such input from RR 420 or I 422 into processor 402 will create a responsive output over line 440 to effect a change, when appropriate, in infant massager 400. Such control over infant massager 400 may preferably involve the processor 402 output signal over line 440 going to controller 450, which responsively initiates the desired change.

Another preferred feature of the invention involves the use of a video camera 460 to monitor the infant being massaged and deliver a digital signal over line 462 to monitor 464, which has screen 466, which can be viewed as part of the remote receiver transmitter RR 420 or be a separate unit viewed directly by a user I 422. Based on what is being observed by the user, further instructions may be provided to processor 402 in the manner described hereinbefore.

During operation, or at selected times, it may be desirable to have the processor 402 emit signals which can be used to create a printout 470 through a signal emitted by a processor 402 over line 471 and/or to provide said signal from said processor 402 for electronic medical data recording and documentation. When any safety concern arises with information which the processor 402 receives, it will be programmed to automatically shut down the massager and provide an audible alarm 472 and/or a visual alarm 474. Under emergency conditions, audible alarms 472 and visual alarms 474 may be activated over lines 473, 475, respectively, if desired. During alarm conditions, the processor 402 may also be programmed to terminate operation of the massager 400.

It will be appreciated, as will be readily known to those skilled in the art, that the controller 450 responsive to signals received from processor 402 will control the timer, which energizes the massager, the actuators, which effect movement of the massaging elements, and the camera 460.

If desired, appropriate signal conditioning and filtering procedures may be employed within processor 402 in a manner well known to those skilled in the art.

The motor (not shown), which is part of the infant massager 400 controlled by the controller 450 will be designed to function at various speeds depending upon the particular program, as well as the forced supply, which serves to adjust the intensity of the massage.

The sensors $S^1$, $S^2$ through $S^N$ may be of whatever number is desired for the particular application. As will be well known to those skilled in the art, the sensors $S^1$, $S^2$ through $S^N$ may be of various types including transducers, which may be of the strain gauge, force/load types, image/visual, motion, position, pressure, audio, optical, electrodes, accelerometers, temperature sensor, brain function monitors, and cardiac respirator monitors employed in order to monitor the infant's physical, behavioral, and physiological response. A sensor may be employed to measure the temperature of the infant's skin during the massage. A sensor may be employed to monitor safety considerations and provide information regarding the same to processor 402.

The cardio respiratory monitor 480 monitors the infant's respiratory and cardiac output and sends information regarding the same to processor 402, which in turn, effects a comparison between the standard stored data and desired values with the actual values. Depending upon the results of the comparison, the processor 402 will or will not emit a signal over line 440 to controller 450 to effect a change in the operation of the massager 400.

In addition to the automatic modification of infant massager 400 operating conditions, the user, through the remote receiver transmitter RR 420 or the input I 422 may, based on information which it receives, effect an immediate shut down of the massager 400 or effect an alteration in the performance of the same. These changes may be effected through controls directly on the infant massager 400 or through the processor 402. The external controls which may deliver signals to the processor 402 or directly to the infant massager 400 may include a keypad (not shown), a power button on/off switch, and other functional buttons, as desired. In addition to the camera 460 displayed on screen 466, the processor 402 may provide a display on screen 466 information regarding the status of the massager or the infant being massaged over line 500 which may be a hard-wired line or a wireless connection.

To use the automated infant massager 400, the infant will be placed in the massager. The infant will be connected to the cardio respiratory monitor 480 and the various sensors $S^1$, $S^2$ through $S^N$ and the device will be turned on. Once turned on, the processor 402 will communicate with memory contained therein to determine and initiate the default settings. For the default settings, the massage elements will not be in contact with the infant's skin. Once the infant is placed in the massager 400 and the massager is turned one, the processor 402 will prompt the user to enter the necessary information using the external control buttons located on the massager or on the wireless remote receiver transmitter RR 420. The user will also be able to enter some of the requested information by using a scanner (not shown) operatively associated with the massager to scan the infant's identification tag. Simultaneously, the processor 402 will initiate the data collection from all sensors $S^1$, $S^2$ through $S^N$ to begin monitoring the infant and controlling the response of the massager 400. The processor 402 and supporting software operatively associated therewith will analyze the data and may display all the results or a portion of the results (relevant information to the user) on the screen 466 to the user. The information collected from the cardio-respiratory monitor 480 will be sent to the processor 402 for analysis and may be displayed to the user on the screen 466. The information entered by the user in addition to the information gathered from the sensors $S^1$, $S^2$ through $S^N$ will be communicated to the processor 402 (and stored in the memory) for analysis to determine the appropriate massage setting (intensity) given, but not limited to, the infant gestational age, birth age, weight, and the like. Once the user selects the start button to approve the massage setting and the appropriate duration, the massage will begin. During the massage, the processor or microcontroller will communicate with all sensors $S^1$, $S^2$ through $S^N$ continuously to coordinate, control, monitor, and modify the intensity of the massage to ensure the effectiveness and safety of the massage based on pre-determined safety parameters and the infant's behavioral and physical response to the stimulus of the massage (monitored by the processor 402 through the sensors). During the massage, if the safety parameters/specifications are not met, the alarm sensors and equipment will be triggered to automatically shut off the massage 400 or reduce the massage intensity to the default setting, and alert a nurse or other professional through alarms 472, 474 that a problem has occurred. If no safety problem arises, the massager will turn off automatically after the specific time which will be monitored by the timer in the processor 402. At the end of the massage, processor may retrieve from the memory information collected during the massage to provide an output signal to the user. The information may provide an overall summary of the massage which will include, but is not limited to, details of the massage, the infant's response, and/or any potential safety problems. This information may be provided, for example, by printout 470, and/or it may be provided directly to a electronic medical records ("EMR") system for electronic documentation.

The massager 400 will be controlled by its operational software. The software will coordinate the communication among all sensors $S^1$, $S^2$ through $S^N$ and controller 450, between the user 422 and the massager 400, and between all sensors $S^1$, $S^2$ through $S^N$ and the processor 402. The software will be primarily responsible for controlling and monitoring the overall function of the massager 400 including but not limited to:

(a) collecting data/information from all sensors $S^1$, $S^2$ through $S^N$ and remote receiver transmitter RR 420 and user I 422;

(b) processing and/or analyzing the data from the sensors $S^1$, $S^2$ through $S^N$ to determine functionality;

(c) monitoring infant condition and adjusting the massage intensity and duration;

(d) data retrieval by outputting/printing out data/information 420 or data transmission for documentation on an electronic medical record system;

(e) analyzing the data from sensors $S^1$, $S^2$ through $S^N$ to determine to access the necessary parameters;

(f) data storage from sensors $S^1$, $S^2$ through $S^N$ users, remote receiver transmitter RR 420, and user I 422, and infant;

(g) initiating and monitoring the alarm system 472, 474;

(h) monitoring and controlling all functions, progress, and decisions making of the massager 400;

(i) coordination of network configuration/use of multiple automated infant massagers by one or more users;

(j) monitoring and enabling manual overrides of the massage settings and massager functions;

(k) have the ability to process all data/information collected from the sensors $S^1$, $S^2$ through $S^N$ to perform the calculations for, but not limited to, determining the weight of the infant, to calculate the forces applied to the infant during the massage, movements by the infant, audio responses of the infant, and facial movements from the infant;

(l) communication with controller 450, user and all sensors $S^1$, $S^2$ through $S^N$, and motors associated with the massager;

(m) initiate operation of actuators; and (n) initiate alarms.

The operational software operatively associated with or disposed within the processor 402 will control the retrieval and analysis of the signals from the all sensors $S^1$, $S^2$ through $S^N$ that monitor the behavioral, physical, and physiological responses from the infant and the data entered by the user, remote receiver transmitter RR 420, and user I 422 to determine the distress state/level of the infant in response to the massage stimulus, the safe progression of the massage, and the proper operation of the massage device. The data will be analyzed and placed on a distress scale that may be based on at least one premature infant pain and/or distress profiles, management, or assessment systems known to those skilled in the art, such as, but not limited to, the PIPP or NIPS. The massager may utilize several different infant pain and/or distress assessment techniques to identify the pain and/or distress level of the infant. The software may give the user the option to choose which assessment techniques they prefer to use for premature infants and full-term infants.

It will be appreciated that, depending upon what is desired to be monitored and the functional objectives, there may be some variation in the apparatus which is provided. For example, a wide variety of sensors may be employed to monitor infant characteristics and massager characteristics described herein and any additional desired monitoring, such as infant temperature, movement of various parts of the infant's body, weight, and the use, for example, of transducers to measure the force applied by the massaging elements.

On the automated infant massager unit itself or on the remote receiver transmitter, or both, user-operated controls may be provided for a variety of purposes, including entering/introducing data regarding a particular infant, programming the system for a particular massage cycle of a particular duration and intensity, on and off controls for the massager, controls to adjust the massage program, controls for initiating an audible or visual alarm or printout, terminating such alarms and printout, and other desired controls. If desired, noninvasive monitoring and measuring of brain activity may be provided with appropriate sensors delivering the information to processor 402. Imaging means, such as near infrared spectroscopy or electromyography ("EMG"), for example, may be employed.

Figure 32:
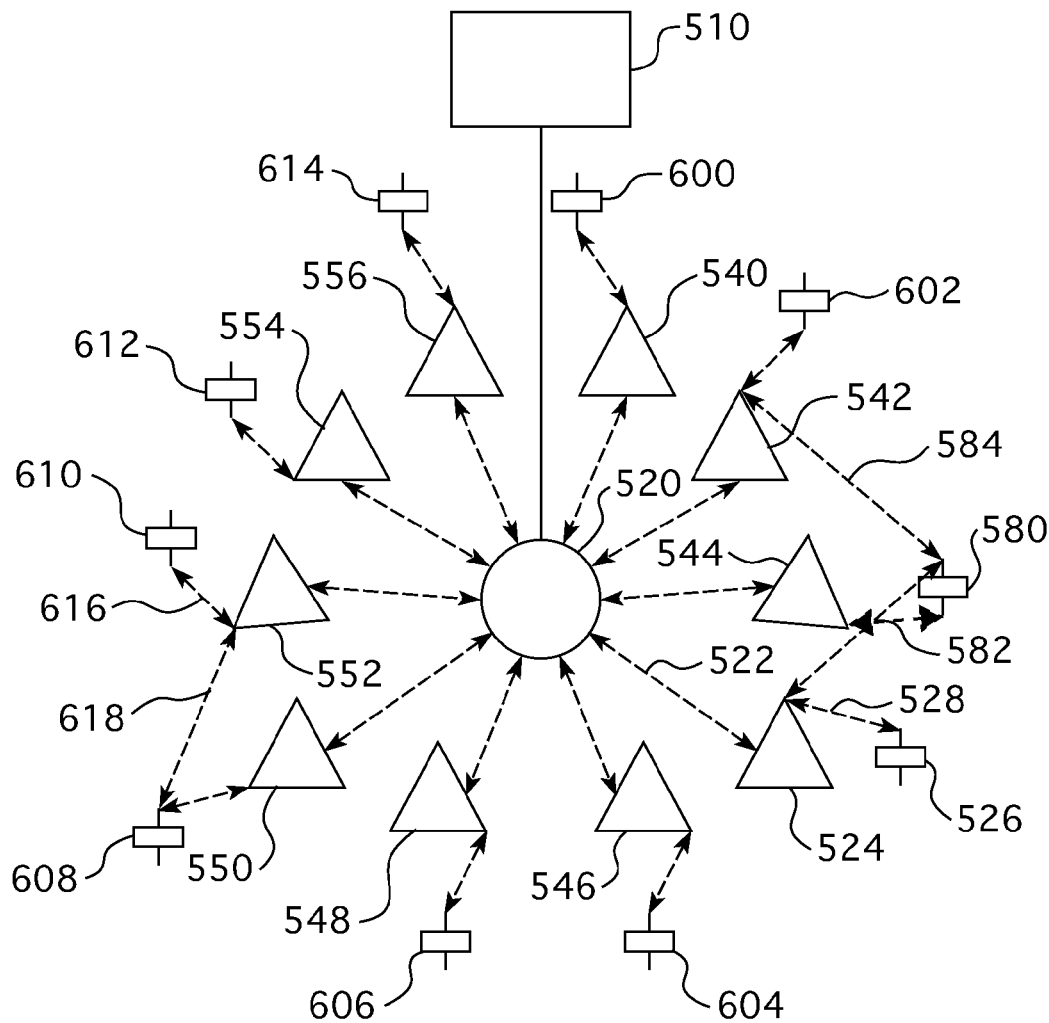
FIG. 32 is a schematic illustration of a network system employable in the present invention.

Referring to FIG. 32, a server 510 is operatively associated with router 520 massager 524, which, in the form shown, is connected to router 520 by wireless connection 522 and is connected to receiver transmitter 526 through wireless connection 528. If desired, a receiver transmitter, such as 580, may be in communication with other automated infant massagers as by connection 582 to infant massager 546 and connection 584 to infant massager 542 to aid the coordination of information flow to the router 520 and network server 510. Similarly, infant massagers, such as 552, may be connected to both receiver/transmitter 608, 610 through the indicated connections 616, 618.

In the form shown, the network contains a plurality of massagers 540, 542, 544, 546, 548, 550, 552, 554, 556, which may cooperate by way of their respective wireless receiver/transmitter 600, 602, 580, 604, 606, 608, 610, 612, 614 with the router 520 in the same manner as massager 544 or in the same manner as massager 548, as indicated by the respective dashed lines. If desired, the communication may go from the massager to the transmitter to the router 520, as will be well known to those skilled in the art.

There may also be additional software and hardware associated with the infant massager 400 (FIG. 31) to coordinate and enable network configuration/usage, monitoring, and operation of one or more massagers by one or more users. A network configuration will allow all massage units to communicate (hard wired or wireless) to a central receiver/transmitter/router 520 which will collect data from the massager concerning the progression of the massage, safety parameters, and the infant's response to the massage. The network configuration would also encompass a database or encompass a means to access a existing patient database that would allow the user to search for infants by name in order to monitor the progress of the infant's response, safety issues, and the progress of the massage. In this embodiment, the software and associated hardware, i.e., a portable wireless controller and/or external controls and the central receiver/transmitter/router, may also be used to communicate with the wireless controller and/or massager to alert the clinician, i.e., doctor or nurse, of any safety problems associated with the massager or the infant, and the termination of massage. The software and hardware for the network configuration may facilitate the storage of data from one or more massagers related to each massaged infant for later data retrieval/printing by the clinician or network server 510. The network configuration software may also encompass the functions listed herein for the non-networked operational software. The networked system configuration can be set up with technology and methods known by those skilled in the art. The network configuration is the preferred embodiment for a clinical setting.

The individual infant massager 400 and the associated apparatus may be employed as a unitary system or may be employed as part of a network, wherein a plurality of such infant massagers 400 is used to massage and monitor a plurality of infants simultaneously by a plurality of users. It may also be employed in network fashion to permit a single user to monitor a plurality of infant massagers operating simultaneously.

Whereas particular embodiments of the invention have been described herein for purposes of illustration, it will be evident to those skilled in the art that numerous variations of the details may be made without departing from the invention as set forth in the appended claims.

The invention claimed is:

1. An automated infant massager system comprising:
    at least one automated infant massager configured to massage an infant,
    an infant support,
    a plurality of movable massage elements structured to underlie at least a portion of the infant being massaged,
    a processor for receiving, and/or measuring, infant information directly or indirectly from said infant massager,
    said infant information including information relating to at least one of the physical, behavioral, and physiological responses of the massaged infant, and
    said processor configured to alter the massage, while the massager is performing a massage, based upon said infant information if it departs from predetermined limits.

2. The automated infant massager system of claim 1 including
    said processor configured to determine from said infant information at least one of the distressed stated and/or pain level of said massaged infant based upon a comparison with data stored within said processor.

3. The automated infant massager system of claim 2 including
    said processor configured to make adjustments to the operation of said massager responsive to said infant information with such adjustment being selected from the group of intensity and duration of said massage.

4. The automated infant massager system of claim 3 including
    said program configured to initiate an alarm if said infant information exceeds predetermined limits.

5. The automated infant massager system of claim 1 including
    a remote receiver transmitter operatively associated with said infant massager and said processor, and
    said remote receiver transmitter being configured to receive infant information from said infant massager and to responsively deliver control signals to said processor or said infant massager.

6. The automated infant massager system of claim 5 including
    a user input configured to deliver signals to at least one system component selected from the group consisting of said processor and said remote receiver transmitter.

7. The automated infant massager system of claim 1 including
    sensors monitoring said infant massager and said infant to provide infant information to said processor regarding at least one condition selected from the group consisting of monitored infant conditions.

8. The automated infant massager system of claim 7 including
    said processor responsive to receipt of said infant information issuing control signals to said infant massager through a controller.

9. The automated infant massager system of claim 5 including
    said remote receiver transmitter configured to receive visual and audible infant information regarding said massaged infant.

10. The automated infant massager system of claim 1 including
    said infant massager being configured to discretely or continuously monitor physical parameters of said infant.

11. The automated infant massager system of claim 1 including
    said infant massager being configured to discretely or continuously monitor behavioral parameters of said infant.

12. The automated infant massager system of claim 1 including
    said infant massager being configured to discretely or continuously monitor physiological parameters of said infant.

13. The automated infant massager system of claim 1 including
    said movable massage elements including a plurality of first movable massage elements structured to underlie at least a portion of said infant,
    a plurality of second movable elements structured to massage at least portions of said infant's arms and legs, and
    a plurality of third massaging elements structured to massage at least a portion of said infant's head.
14. The automated infant massager system of claim 1 including
    said plurality of movable massage elements structured to assume a first expanded position for more intimate contact with said infant and a second compressed position for less intimate contact with said infant.
15. The automated infant massager system of claim 14 including
    said processor configured to emit control signals to adjust said plurality of massage elements to provide for positioning of said massage elements in said first expanded position, said second compressed position, and positions therebetween based upon infant information received by said processor or input from a user.
16. The automated infant massager system of claim 1 including
    said infant massager having a brow monitor securable to said infant's forehead for monitoring brow movement.
17. The automated infant massager system of claim 1 including
    a video camera for providing an image of said infant and a screen for displaying images of said infant.
18. The automated infant massager system of claim 1 including
    an audio pickup for permitting at least one of a user and/or said processor to monitor sounds emitted by said infant.
19. The automated infant massager system of claim 7 including
    said sensors including sensors which monitor at least one parameter selected from the group consisting of facial movement, brow movement, mouth clenching actions or reactions of the limbs or the body to external stimuli, movement of arms, movement of legs, wiggling, heart rate, breathing rate, brain activity, crying, sleeping, arousal state, respiratory rate, blood pressure, safety parameters, and massager shutdown.
20. The automated infant massager system of claim 1 including
    said processor being configured to employ said infant information to determine an infant's condition and said processor being configured to emit a control signal to adjust the intensity or duration of the massage responsive to an indication that there has been a departure from desired infant conditions.
21. The automated infant massager system of claim 14 including
    said processor being configured to adjust at least one parameter selected from the group consisting of the speed of movement of said massage elements and the expanded or compressed state of said massage elements.
22. The automated infant massager system of claim 1 including
    said processor configured to terminate or adjust operation of said infant massager if the monitored physical, behavioral, or physiological responses depart from desired levels as indicated by comparison of infant information with data stored within said processor.
23. The automated infant massager system of claim 1 including
    user-operable controls for effecting calibration and control of operation of said infant massager disposed on or closely adjacent to said infant massager or disposed on a remote control receiver.
24. The automated infant massager system of claim 23 including
    said controls permitting user override of processor control signals.
25. The automated infant massager system of claim 1 including
    said processor being configured to be calibrated for the desired infant massage for each infant.
26. The automated infant massager system of claim 1 including
    said processor configured to turn off said massager if monitored infant parameters exceed certain desired levels as determined by comparing said infant information with data stored within said processor.
27. The automated infant massager system of claim 26 including
    said monitored infant parameters including safety parameters.
28. The automated infant massager system of claim 26 including
    said processor configured to initiate an alarm in the event of said turning off of the massager.
29. The automated infant massager system of claim 16 including
    said processor being configured to employ the output of said brow monitor to determine distress and pain level of said massaged infant.
30. The automated infant massager system of claim 1 including
    said processor being configured to emit sounds which are delivered to said massaged infant through a speaker.
31. The automated infant massager system of claim 1 including
    said infant massager having a cover which will provide a boundary between the massaged infant's body and said massage elements.
32. The automated infant massager system of claim 1 including
    said processor being part of a network which controls operation of a plurality of infant massagers which are structured to simultaneously massage a plurality of infants.
33. The automated infant massager system of claim 13 including
    at least some of said movable massage elements being encapsulated.
34. The automated infant massager system of claim 31 including
    said cover having a plurality of slits for permitting the massage elements to pass therethrough.
35. The automated infant massager system of claim 34 including
    said network includes a processor which is operatively associated with a router, which in turn, is operatively associated with a plurality of said infant massagers.
36. The automated infant massager system of claim 35 including
    said router being operatively associated with at least one unit selected from the group consisting of a network server and an electronic medical record system.

37. The automated infant massager system of claim 1 including
said automated infant massager system being configured to communicate, receive, and send information to an electronic medical record system.

38. The automated infant massager system of claim 33 including
said infant massagers being controllable by at least one of said processor and a user.

39. The automated infant massager system of claim 38 including
said processor being configured to store information regarding each said infant massager and to process infant information separately for each said infant massager.

40. The automated infant massager system of claim 39 including
said processor being configured to store and process information to be delivered to an electronic medical record system.

41. The automated infant massager system of claim 1 including
said infant massager being configured to allow a user to enter information into said infant massager and said processor by scanning an identification tag or an identification bar code associated with said massaged infant.

42. The automated infant massager system of claim 41 including
said infant massager and, processor being configured to receive information signals about the infant through the scanning of an identification tag.

43. The automated infant massager system of claim 42 including
said identification tag being a tag selected from the group consisting of a radio-frequency identification tag and a bar code tag.

44. The automated infant massager system of claim 1 including
said system configured to be employed with at least one infant selected from the group consisting of premature infants and full-term infants.

45. The automated infant massager system of claim 1 including
a plurality of sensors for monitoring at least one of (a) operation of said automated infant massager and (b) said infant, and
a feedback system for receiving information from said sensors and delivering the same to said processor.

* * * * *